(12) United States Patent
Meguro et al.

(10) Patent No.: US 8,003,645 B2
(45) Date of Patent: Aug. 23, 2011

(54) PREVENTIVES OR REMEDIES FOR ALZHEIMER'S DISEASE, OR AMYLOID PROTEIN FIBRIL-FORMATION INHIBITORS, WHICH INCLUDE A NITROGEN-CONTAINING HETEROARYL COMPOUND

(75) Inventors: Masaki Meguro, Tokyo (JP); Tomichiro Oda, Tokyo (JP); Yasuhiro Nakagami, Tokyo (JP); Shinji Marumoto, Tokyo (JP); Kazuo Koyama, Tokyo (JP); Isao Kaneko, Tokyo (JP)

(73) Assignee: BTG International Ltd., London (GB)

( * ) Notice: Subject to any disclaimer, the term of this patent is extended or adjusted under 35 U.S.C. 154(b) by 167 days.

(21) Appl. No.: 12/068,407

(22) Filed: Feb. 6, 2008

(65) Prior Publication Data
US 2008/0182846 A1    Jul. 31, 2008

Related U.S. Application Data

(62) Division of application No. 10/497,183, filed as application No. PCT/JP02/12265 on Nov. 25, 2002, now Pat. No. 7,589,105.

(30) Foreign Application Priority Data

Nov. 28, 2001 (JP) .................. 2001-361847
Jul. 2, 2002 (JP) .................. 2002-192777

(51) Int. Cl.
C07D 251/00 (2006.01)
C07D 251/18 (2006.01)
C07D 251/48 (2006.01)
(52) U.S. Cl. ............ 514/245; 544/180; 544/208
(58) Field of Classification Search ........... 514/245; 544/180, 208
See application file for complete search history.

(56) References Cited

U.S. PATENT DOCUMENTS 2,393,755 A * 1/1946 D Alelio ............ 544/197
6,335,339 B1 * 1/2002 Arenas et al. ............ 514/245

FOREIGN PATENT DOCUMENTS

| WO | WO 95/15952 | 6/1995 |
|---|---|---|
| WO | WO 97/19065 | 5/1997 |
| WO | WO 00/12485 A | 3/2000 |
| WO | WO 01/25220 | 4/2001 |
| WO | WO 01/55093 A | 8/2001 |

OTHER PUBLICATIONS

Ghosh, Journal of Medical Chemistry, vol. 10, No. 5, 1967, pp. 974-975, XP001000379.
Nakagami, British Journal of Pharmacology, vol. 137, No. 5, 2002, pp. 676,682, XP002347488.
Kakagami, European Journal of Pharmacology, vol. 457, No. 1, 2002, pp. 11-17, XP002347489.
Tschanz et al; "Alzheimer's: Just a memory?", *Research Matters 2006 Publication*; pp. 16-19.

* cited by examiner

*Primary Examiner* — Marcos Sznaidman
(74) *Attorney, Agent, or Firm* — Nixon & Vanderhye

(57) ABSTRACT

The present invention relates to preventives or remedies for Alzheimer's disease, or to amyloid protein fibril-formation inhibitors, which include as an active ingredient a compound of general formula (I) below or a pharmacologically permitted salt thereof; and also to nitrogen-containing heteroaryl derivatives having specific substituents, or pharmacologically permitted salts thereof, which are valuable as preventives or remedies for Alzheimer's disease, or as amyloid protein fibril-formation inhibitors:

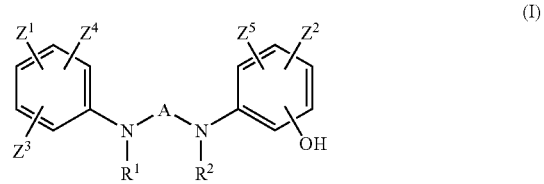

(where, $R^1$ and $R^2$ are H or alkyl; $Z^1$ and $Z^2$ are H, alkyl, alkoxy, haloalkyl or halogeno; $Z^3$ is alkoxy, SH, alkylthio, $NH_2$, mono- or di-alkylamino, OH or halogeno; $Z^4$ and $Z^5$ are H or halogeno; and A is 4,6-pyrimidine-1,3-diyl, 1,3,5-triazine-2,6-diyl, etc).

11 Claims, No Drawings

PREVENTIVES OR REMEDIES FOR ALZHEIMER'S DISEASE, OR AMYLOID PROTEIN FIBRIL-FORMATION INHIBITORS, WHICH INCLUDE A NITROGEN-CONTAINING HETEROARYL COMPOUND

This application is a divisional of application Ser. No. 10/497,183, filed Oct. 19, 2004, now U.S. Pat. No. 7,589,105 which is a 371 of PCT/JP02/12265, filed 25 Nov. 2002, the entire content of which is hereby incorporated by reference in this application.

TECHNICAL FIELD

The present invention relates to preventives or remedies for Alzheimer's disease and to amyloid protein fibril-formation inhibitors which include at least one nitrogen-containing heteroaryl compound or physiologically-permitted salt thereof as an active ingredient.

Furthermore, the present invention also relates to nitrogen-containing heteroaryl derivatives with specified substituents which are valuable as preventives or remedies for Alzheimer's disease, or as amyloid protein fibril-formation inhibitors.

TECHNICAL BACKGROUND

β-Amyloid protein (hereinafter referred to as Aβ) is a major structural component of the senile plaques strikingly present in the brains of patients with Alzheimer's disease, and it is an insoluble peptide comprising 39 to 43 amino acids. It is produced by enzymic cleavage from β-amyloid protein precursor protein.

From recent detailed pathological research into the brains of patients with Alzheimer's disease it is reported that, in the process of the occurrence of dementia, first of all there is a build-up of Aβ within the brain of the patient, which triggers the formation of senile plaques, and after the passage of a considerable number of years there occurs neurofibrillary degeneration followed by neuronal degenerative loss [Ann. Rev. Neurosci., Vol. 12, 463 (1989)]

Furthermore, it is reported that Aβ which comprises 40 amino acids (Aβ1-40) and its active central portion peptide (Aβ 25-35) cause degeneration and death of rat primary hippocampal neurons in an in vitro experimental system and specifically lower the cellular MTT [3-(4,5-dimethylthiazol-2-yl)-2,5-diphenyl tetrazolium bromide] reduction capacity [see, respectively, Science, Vol. 250, 279 (1990) and J. Neurochem., Vol. 65, 2585 (1995)].

As examples of the cells exhibiting a lowering of the MTT reduction capacity due to Aβ, there are foetal rat hippocampal neurons, PC12 cells and HeLa cells, etc. Consequently, by measuring activity in inhibiting this lowering of the MTT reduction capacity due to Aβ in such cells, it is possible to investigate substances which inhibit the damaging action of Aβ on nerve cells.

Now, long-term potentiation (hereinafter referred to as LTP) is a phenomenon in which, by hippocampal nerve fibre electrical stimulation at high frequency for a short time, the synapse reaction strength is increased over a prolonged period, and it is regarded as a model for learning and memory. It is reported that, in hippocampal sections, Aβ has an LTP impairing action [J. Neurosci. Res. Vol. 60, 65 (2000), Proc. Natl. Acad. Sci. USA, Vol. 95, 6448 (1998), etc]. Furthermore, it is reported that, in a transgenic mouse overexpressing Aβ, LTP in the hippocampus is inhibited compared to normal mouse and, in a learning behaviour test, the memory and learning capacity are lowered [Science, Vol. 274 99 (1996)].

Consequently, by investigating substances which inhibit LTP impairment due to Aβ in the hippocampus, it is possible to investigate substances which lessen memory impairment caused by Aβ.

Aβ is regarded as at least one of the causes of the occurrence of Alzheimer's disease, so a substance which inhibits the impairment of nerve cells induced by Aβ would be effective as a preventive or remedy for Alzheimer's disease.

Examples of known compounds which suppress nerve cell toxicity due to Aβ are rifampicin [Biochem. Biophys. Res. Commun., Vol. 204, 76 (1994)], Congo Red [Proc. Natl. Acad. Sci. USA, Vol. 91, 12243 (1994) and AZ36041 [Biol. Pharm. Bull., Vol. 18, 1750 (1995), etc.

Moreover, (−)-huperzine A is an example of a compound reported to suppress LTP impairment in the hippocampus due to Aβ [Neurosci. Lett. Vol. 275 (3): 187-190 (1999)].

Illnesses which are characterised by the extracellular deposition in various organs and tissues of polymerized amyloid protein which adopts a specific fibrillar structure are generally classified as amyloidosis. The protein from which this amyloid is composed is, for example, in Alzheimer's disease, Aβ which is deposited in the brain; in type 2 diabetes, it is amylin which is deposited in the pancreas; in familial amyloid neuropathy, it is serum prealbumin (transthyretin) which is deposited in the peripheral nerves; it is immunoglobulin light chain-derived AL protein in the case of amyloidosis accompanying primary and multiple myeloma; and it is AA protein in the case of secondary amyloidosis, etc. [See, for example, Sipe, J. D., Annu. Rev. Biochem., Vol. 61, 947-97 (1992), etc.]

The fact that the amyloid protein in the course of fibril-formation produces a β-sheet structure is known to be a characteristic common to many amyloid proteins. [See, for example, Sipe, J. D., Annu. Rev. Biochem., Vol. 61, 947-97 (1992), etc.]

Aβ is a typical amyloid protein, and it accumulates in the brains of Alzheimer's disease patients, forming senile plaques. Within the senile plaques, a β-sheet structure is adopted and fibril formation occurs, and there is known to be characteristic staining by dyes such as thioflavin and Congo red which denote a fibrillar structure. Furthermore, it is known that with the adoption of the β-sheet structure and fibril formation, Aβ shows toxicity to cultured nerve cells [Pike, C. J. et al, J. Neurosci. Vol. 13, 1676-1687 (1993)]

It is also known that the amylin, which is the main structural component of the amyloid protein deposited in the pancreas in type 2 diabetes, adopts a β-sheet structure and forms fibrils, which show toxicity to pancreatic β-cells [Lorenzo, A. et al, Nature, Vol. 368, 756-760 (1994)].

It is reported that amyloid proteins such as Aβ and amylin both exhibit cytotoxicity by adopting a β-sheet structure and forming fibrils, and by lowering the cell MTT reduction capacity. Consequently, it is thought that compounds which inhibit this fibril formation by amyloid proteins like Aβ and amylin would inhibit their cell toxicity. Furthermore, since the mechanism of such manifestation of cytotoxicity is common to a number of amyloid proteins, it is believed that drugs which inhibit the cytotoxicity of certain amyloid proteins and suppress fibril-formation could also inhibit cytotoxicity and fibril-formation in other amyloid proteins.

Thus, as well as Alzheimer's disease and type 2 diabetes, by suppressing fibril-formation of amyloid protein this will be effective as a preventive or remedy for, for example, immunoglobulinic amyloidosis, reactive amyloidosis, familial amyloidosis, dialysis-related amyloidosis, senile amyloidosis, cerebrovascular amyloidosis, hereditary cerebral hemorrhage with amyloidosis, Creutzfeldt-Jakob disease, bovine spongiform encephalitis (BSE), scrapie, medullary carcinoma of the thyroid, insulinoma, localized atrial amyloid, amyloidosis cutis, localized nodular amyloidosis and other types of amyloidosis, preferably for Alzheimer's disease, type 2 diabetes, dialysis-related amyloidosis, familial amyloidosis, Creutzfeldt-Jakob disease and BSE, and in particular for Alzheimer's disease or type 2 diabetes.

Known examples of compounds which inhibit amyloid protein fibril-formation include variant peptide (WO96/28471), imino-aza-anthracyclinone derivatives derived from anthrazalone (WO98/32754), thionaphthalene derivatives with a specific structure (JP-A-9-95444) and isochroman compounds (JP-A-2000-198781). As compounds which inhibit fibril-formation by Aβ in particular from amongst the amyloid proteins, there are known iAβ5 [Nat. Med., Vol. 4, 822-826 (1998)], and PTI-00703 [Neurobiol. Aging, Vol. 19 (Suppl 4) 1070 (1998). However, these compounds have a structure which is completely different from the nitrogen-containing heteroaryl compounds which are the effective component of the amyloid protein fibril-formation inhibitors of the present invention.

With regard to nitrogen-containing heteroaryls, 3-[[4-[(2-fluoro-5-methylphenyl)amino]-2-pyrimidinyl]amino]-phenol and 4-[[6-[(2,5-dichlorophenyl)amino]-4-pyrimidinyl]amino]-phenol are disclosed as having an anticancer action (WO00/12485, WO00/12486, etc), and the analogous 4,6-dianilino-pyrimidine derivatives are also disclosed as having an anticancer action (Japanese Patent Publication (PTC) No. 9-506363). Moreover, 4,4'-[(6-methyl-2,4-pyrimidinediyl)diimino]bisphenol, 4,4'-[(6-amino-1,3,5-triazine-2,4-diyl)diimino]bisphenol and 4,4'-[2,4-pyrimidinediyldiimino]bisphenol are disclosed as having an antibacterial action or anti-HIV action [J. Indian Chem. Soc. Vol. 58 [5], 512-13 (1981), Acta Cienc. Indica. Chem. Vol. 11[1], 66-70 (1985), J. Med. Chem. Vol. 9(3), 423-4, (1966), WO99/36410, WO99/50250].

Moreover, it has been disclosed that triazine derivatives with a 4-position derivative have an impeding action for kinase which is an enzyme catalysing the reaction to produce ATP by transfer of a phosphoryl group within the cell, and are valuable in the treatment of Alzheimer's disease, etc (WO01/25220).

DISCLOSURE OF THE INVENTION

The present inventors have carried out a painstaking study with the objective of developing preventives or remedies for Alzheimer's disease which have powerful activity and are highly safe, and they have discovered that nitrogen-containing heteroaryl compounds have an outstanding action in inhibiting the lowering of MTT reduction capacity and in inhibiting long-term potentiation impairment in the hippocampus, and are useful as preventives or remedies for Alzheimer's disease. The present invention has been perfected based on this discovery.

Furthermore, the present inventors have also carried out a painstaking study with the objective of developing highly active and highly safe drugs which can suppress amyloid protein fibril-formation and can suppress cytotoxicity brought about by the amyloid protein, and they have discovered that nitrogen-containing heteroaryl compounds have an outstanding inhibitory action in terms of amyloid protein fibril-formation, and also have a fibrillar amyloid protein breakdown action and are valuable as preventives or remedies for amyloidosis, for example Alzheimer's disease and type 2 diabetes. The present invention has also been perfected based on this discovery.

This invention provides preventives or remedies for Alzheimer's disease, or amyloid protein fibril-formation inhibitors, which include at least one nitrogen-containing heteroaryl compound, or pharmacologically permitted salt thereof, as an active ingredient.

It also provides nitrogen-containing heteroaryl derivatives which possess specified groups.

Specifically, the nitrogen-containing heteroaryl compounds which are an active ingredient of the Alzheimer's disease preventives or remedies, or of the amyloid protein fibril-formation inhibitors, of the present invention, have the following general formula

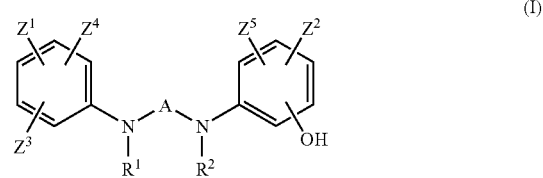

In this formula, $R^1$ and $R^2$ each independently represent a hydrogen atom or a $C_{1-6}$ alkyl group, $Z^1$ and $Z^2$ each independently represent a hydrogen atom, $C_{1-6}$ alkyl group, $C_{1-6}$ alkoxy group, halo-$C_{1-6}$ alkyl group or halogen atom, $Z^3$ represents a $C_{1-6}$ alkoxy group, mercapto group, $C_{1-6}$ alkylthio group, amino group, mono- or di-$C_{1-6}$ alkylamino group, hydroxy group or halogen atom, $Z^4$ and $Z^5$ each independently represent a hydrogen atom or halogen atom, and A represents a group of formula (II) to (VI) below.

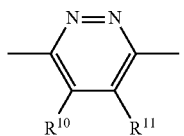

(VI)

In formulae (II) to (VI) above,
$R^3$ represents a hydrogen atom, $C_{1-6}$ alkyl group, $C_{1-6}$ alkoxy group, mercapto group, $C_{1-6}$ alkylthio group, amino group, mono- or di-$C_{1-6}$ alkylamino group or hydroxy group,
$R^4$ represents a hydrogen atom or nitro group,
$R^5$ represents a hydrogen atom or $C_{1-6}$ alkyl group,
$R^6$ represents a hydrogen atom, $C_{1-6}$ alkyl group, $C_{1-6}$ alkoxy group, mercapto group, $C_{1-6}$ alkylthio group, amino group, mono- or di-$C_{1-6}$ alkylamino group or hydroxy group,
$R^7$ and $R^8$ each independently represent a hydrogen atom, $C_{1-6}$ alkyl group, $C_{1-6}$ alkoxy group, mercapto group, $C_{1-6}$ alkylthio group, amino group or mono- or di-$C_{1-6}$ alkylamino group,
$R^9$ represents a $C_{1-6}$ alkyl group, $C_{1-6}$ alkoxy group, mercapto group, $C_{1-6}$ alkylthio group, amino group, mono- or di-$C_{1-6}$ alkylamino group or hydroxy group, and
$R^{10}$ and $R^{11}$ each independently represent a hydrogen atom, $C_{1-6}$ alkyl group, $C_{1-6}$ alkoxy group, $C_{1-6}$ alkylthio group, or mono- or di-$C_{1-6}$ alkylamino group.

Furthermore, amongst the compounds (I), the nitrogen-containing heteroaryl derivatives of the following general formula (VII) below

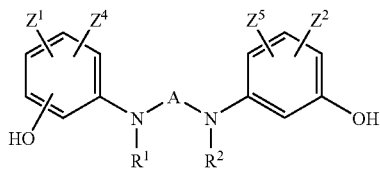

(VII)

or general formula (VIII) below

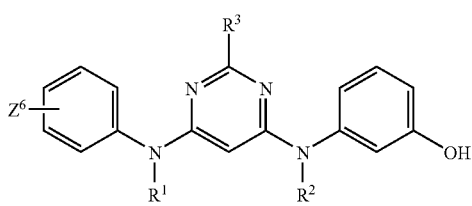

(VIII)

are novel compounds.

In the above formulae, $R^1$, $R^2$, $R^3$, $Z^1$, $Z^2$, $Z^4$, $Z^5$ and A have the same meanings as above, and $Z^6$ represents a $C_1$-$C_6$ alkoxy group or a halogen atom.

The "$C_1$-$C_6$ alkyl group" denoted by $R^1$, $R^2$, $R^3$, $R^4$, $R^5$, $R^6 R^8$, $R^9$, $R^{10}$, $R^{11}$, $Z^1$ and $Z^2$, or the $C_1$-$C_6$ alkyl portion of the "$C_1$-$C_6$ alkoxy group" denoted by $R^3$, $R^7$, $R^8$, $R^9$, $Z^1$, $Z^2$, $Z^3$ and $Z^6$ may be, for example, a methyl, ethyl, propyl, isopropyl, butyl, isobutyl, s-butyl, t-butyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl or 1,2,2-trimethylpropyl group. Excepting the alkyl group and the alkyl portion of the alkoxy group in the definitions of $R^1$, $R^2$, $R^3$, $R^9$, $R^{10}$ and $R^{11}$, and the alkyl portion of the alkoxy group in the definitions of $R^6$ and $Z^3$, it is preferably a $C_{1-4}$ alkyl group, more preferably a methyl or ethyl group, and in particular a methyl group.

The alkyl group and the alkyl portion of the alkoxy {sic} group in the definitions of $R^1$ and $R^2$ are preferably a methyl or ethyl group.

The alkyl group in the definition of $R^3$ is preferably a $C_{1-5}$ alkyl group, more preferably a $C_{1-4}$ alkyl group, and still more preferably an ethyl, propyl or isopropyl group. The alkyl portion of the alkoxy group in the definition of $R^3$ is preferably a $C_{1-4}$ alkyl group and more preferably a $C_{1-3}$ alkyl group.

The alkyl portion of the alkoxy group in the definition of $R^6$ is preferably a $C_{1-3}$ alkyl group, and more preferably a methyl or ethyl group.

The alkyl group in the definition of $R^9$ is preferably a $C_{1-5}$ alkyl group, more preferably a $C_{2-4}$ alkyl group and still more preferably an ethyl, propyl, isobutyl, s-butyl or t-butyl group. The alkyl portion of the alkoxy group in the definition of $R^9$ is preferably a $C_{1-4}$ alkyl group, more preferably a methyl, ethyl or butyl group, and in particular a butyl group.

The alkyl group and the alkyl portion of the alkoxy group in the definitions of $R^{10}$ and $R^{11}$ are preferably a $C_{1-3}$ alkyl group.

The alkyl portion of the alkoxy group in the definition of $Z^3$ is preferably a $C_{1-3}$ alkyl group.

The "halogen atom" in the definitions of $Z^1$, $Z^2$, $Z^3$, $Z^4$, $Z^5$ and $Z^6$ is for example a fluorine, chlorine, bromine or iodine atom, preferably a fluorine or chlorine atom, and in particular a chlorine atom.

The $C_{1-6}$ alkyl portion of the "halo-$C_{1-6}$ alkyl group" in the definitions of $Z^1$ and $Z^2$ is the same as in the case of the $C_{1-6}$ alkyl group above, and the halogen portion is the same as the halogen atom above. Examples are the fluoromethyl, difluoromethyl, trifluoromethyl, chloromethyl, dichloromethyl, trichloromethyl, 1-fluoroethyl, 2-fluoroethyl, 1,1-difluoroethyl, 1,2-difluoroethyl, 1-chloroethyl, 2-chloroethyl, 1,1-dichloroethyl and 1,2-dichloroethyl group, with the fluoromethyl, difluoromethyl, trifluoromethyl, chloromethyl, dichloromethyl, trichloromethyl, 1-fluoroethyl and 1-chloroethyl group being preferred, and the trifluoromethyl group further preferred.

The $C_{1-6}$ alkyl portion of the "$C_{1-6}$ alkylthio group" in the definitions of $R^3$, $R^6$, $R^7$, $R^8$, $R^9$, $R^{10}$, $R^{11}$ and $Z^3$ is the same as the $C_{1-6}$ alkyl group above, and examples are methylthio, ethylthio, propylthio, isopropylthio, butylthio, isobutylthio, s-butylthio and t-butylthio.

Excluding the alkyl portion of the thioalkyl group in the definitions of $R^3$, $R^6$, $R^{10}$, $R^{11}$ and $Z^3$, a $C_{1-4}$ alkylthio is preferred, more preferably the methylthio or ethylthio group, and in particular the methylthio group.

With regard to the alkyl portion of the thioalkyl group in the definitions of $R^3$, $R^6$, $R^{10}$, $R^{11}$ and $Z^3$ this is preferably a $C_{1-3}$ alkyl group, with the methylthio group being particularly preferred.

The $C_{1-6}$ alkyl portion of the "mono- or di-$C_{1-6}$ alkylamino group" in the definitions of $R^3$, $R^6$, $R^7$, $R^8$, $R^9$, $R^{10}$, $R^{11}$ and $Z^3$ is the same as the $C_{1-6}$ alkyl group above, examples being the methylamino, ethylamino, propylamino, dimethylamino, methylethylamino, methylpropylamino, diethylamino, ethylpropylamino and dipropylamino groups. Except in the case of $R^3$ and $R^9$, the methylamino, ethylamino or dimethylamino group is preferred, with the methylamino group particularly preferred. With regard to the mono- or di-alkylamino group in the definitions of $R^3$ and $R^9$, a mono- or di-$C_{1-3}$ alkylamino group is preferred, and methylamino or dimethylamino is further preferred.

$Z^3$ is preferably a $C_{1-4}$ alkoxy group, $C_{1-4}$ alkylthio group or hydroxy group, more preferably a $C_{1-2}$ alkoxy group, $C_{1-2}$ alkylthio group or hydroxy group, with a hydroxy group particularly preferred.

In the case of the compounds of the present invention represented by general formula (I) or (VII) above, the following preferred compounds can be cited.

1) The compounds where $R^1$ and $R^2$ are each independently a hydrogen atom or a $C_{1-2}$ alkyl group,
2) The compounds where $R^1$ and $R^2$ are hydrogen atoms,
3) The compounds where A is a group represented by formula (II) (where $R^3$ is a hydrogen atom, $C_{1-5}$ alkyl, $C_{1-3}$ alkylthio or mono- or di-$C_{1-3}$ alkylamino group, and $R^4$ is a hydrogen atom or nitro group), a group represented by formula (III) (where $R^5$ and $R^6$ are each independently a hydrogen atom or $C_{1-2}$ alkyl group), a group of formula (IV) (where $R^7$ and $R^8$ are each independently a hydrogen atom or $C_{1-2}$ alkyl group), a group of formula (V) (where $R^9$ is a $C_{1-5}$ alkyl, $C_{1-4}$ alkoxy or a $C_{1-4}$ alkylthio group), or a group of formula (VI) (where $R^{10}$ and $R^{11}$ are each independently a hydrogen atom or $C_{1-3}$ alkyl group),
4) The compounds where A is a group of formula (II) (where $R^3$ is a hydrogen atom, $C_{1-5}$ alkyl, $C_{1-3}$ alkylthio or mono- or di-$C_{1-3}$ alkylamino group, and $R^4$ is a hydrogen atom or nitro group), a group of formula (III) (where $R^5$ is a hydrogen atom and $R^6$ is a methyl or ethyl group), a group of formula (IV) (where $R^7$ and $R^8$ are hydrogen atoms), a group of formula (V) (where $R^9$ is a $C_{1-5}$ alkyl, $C_{1-4}$ alkoxy or $C_{1-4}$ alkylthio group), or a group of formula (VI) (where $R^{10}$ and $R^{11}$ are hydrogen atoms),
5) The compounds where A is a group of formula (II) (where $R^3$ is a hydrogen atom, $C_{1-4}$ alkyl or amino group, and $R^4$ is a hydrogen atom or nitro group) or a group of formula (V) (where $R^9$ is a $C_{2-4}$ alkyl or a butoxy group),
6) The compounds where A is a group of formula (II) (where $R^3$ is an ethyl, propyl, isopropyl or amino group and $R^4$ is a hydrogen atom, or $R^3$ is a hydrogen atom and $R^4$ is a nitro group) or a group of formula (V) (where $R^9$ is a $C_{2-4}$ alkyl group),
7) The compounds where $Z^1$ and $Z^2$ are each independently a hydrogen atom or para-position fluorine atom, chlorine atom or $C_{1-2}$ alkyl group,
   $Z^3$ is a meta-position hydroxy group (in the case of compound (I)), or the hydroxy group on the phenyl ring to which $Z^1$ is bonded is in the meta-position (in the case of compound (VII)) and
   $Z^4$ and $Z^5$ are hydrogen atoms,
8) The compounds where $Z^1$ and $Z^2$ are each a hydrogen atom or para-position methyl group,
   $Z^3$ is a meta-position hydroxy group (in the case of compound (I), or the hydroxy group on the phenyl ring to which $Z^1$ is bonded is in the meta-position (in the case of compound (VII)), and
   $Z^4$ and $Z^5$ are hydrogen atoms.

Taking these together, for example combinations of 2), 3) to 6) and 8) are preferred. Amongst these combinations, the combination of 2), 6) and 8) is further preferred.

Moreover, in the case of the compounds (VIII), there can be cited 1) the compounds where $R^1$ and $R^2$ are each independently a hydrogen atom or $C_{1-2}$ alkyl group,
2) the compounds where $R^1$ and $R^2$ are hydrogen atoms,
3) the compounds where $R^3$ is a hydrogen atom, $C_{1-5}$ alkyl, $C_{1-3}$ alkylthio, mono- or di-$C_{1-3}$ alkylamino group or amino group,
4) the compounds where $R^3$ is a hydrogen atom, $C_{1-4}$ alkyl or amino group,
5) the compounds where $R^3$ is an ethyl, propyl, isopropyl or amino group,
6) the compounds where $Z^6$ is a $C_{1-4}$ alkoxy group, fluorine atom or chlorine atom, and
7) the compounds where $Z^6$ is a methoxy group, ethoxy group or chlorine atom.

Taking these together, for example combinations of 2), 3) to 5) and 7) are preferred. Amongst these combinations, the combination of 2), 5) and 7) is further preferred.

The compounds of the present invention of general formula (I), (VII) or (VIII) possess within the same molecule a phenolic hydroxy group, which is a weakly acidic group, and an amino group or alkylamino group, etc, which is a weakly basic group, so they form physiologically permitted salts when reacted with a comparatively strong base or acid. Examples of such salts are the salts with a base, such as alkali metal salts like the lithium salt, sodium salt and potassium salt, alkaline earth metal salts like the magnesium salt, calcium salt and barium salt, and amino acid salts like the glycine salt, lysine salt, arginine salt, ornithine salt, glutamic acid salt and aspartic acid salt. The alkali metal salts are preferred (in particular the sodium salt).

Furthermore, examples of the salts with an acid are mineral acid salts like hydrohalide salts such as the hydrochloride, hydrobromide and hydroiodide, the nitrate, perchlorate, sulphate, phosphate and carbonate, sulphonic acid salts like the methanesulphonate, trifluoromethanesulphonate, ethanesulphonate, benzene-sulphonate and toluenesulphonate, and carboxylic acid salts such as the acetate, fumarate and maleate. The hydrochloride, nitrate, sulphate and phosphate are preferred.

Moreover, where the compounds of the present invention and their pharmacologically permitted salts form solvates (such as hydrates), then these too are included within the scope of the invention.

Tables 1 to 5 below give specific examples of preferred compounds represented by aforesaid general formulae (I), (VII) or (VIII). The compounds shown in Tables 1 to 5 have the formulae denoted by (1) to (5) respectively.

With regard to the abbreviations employed below, Me means the methyl group, Et means the ethyl group, Pr means the propyl group, iPr means the isopropyl group, Bu means the butyl group, iBu means the isobutyl group, sBu means the s-butyl group, tBu means the t-butyl group, Pn means the pentyl group and Hx means the hexyl group.

The compounds of the following general formula

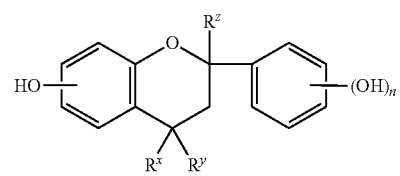

[where $R^x$, $R^y$ and $R^z$ are the same or different, and each represent a hydrogen atom or a $C_{1-4}$ alkyl group (preferably $R^x$, $R^y$ and $R^z$ are the same or different, and each represent a hydrogen atom or a methyl group; more preferably, $R^x$, $R^y$ and $R^z$ are methyl groups), and n is 1 or 2 (preferably 2)] are known compounds (see, for example, JP-A-5-32654), and possess an outstanding action in inhibiting a lowering of the MTT reduction capacity and in inhibiting LTP impairment in the hippocampus, and they are valuable as Alzheimer's disease preventives or remedies.

TABLE 1

(1)

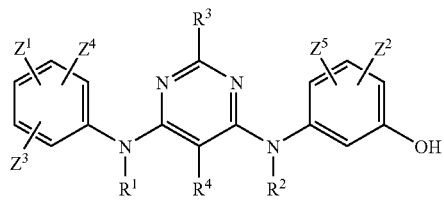

| Exemplified Compound No. | $R^1$ | $R^2$ | $R^3$ | $R^4$ | $Z^1$ | $Z^2$ | $Z^3$ | $Z^4$ | $Z^5$ |
|---|---|---|---|---|---|---|---|---|---|
| 1-1 | H | H | H | H | H | H | 3-OH | H | H |
| 1-2 | H | H | Me | H | H | H | 3-OH | H | H |
| 1-3 | H | H | Et | H | H | H | 3-OH | H | H |
| 1-4 | H | H | Pr | H | H | H | 3-OH | H | H |
| 1-5 | H | H | iPr | H | H | H | 3-OH | H | H |
| 1-6 | H | H | Bu | H | H | H | 3-OH | H | H |
| 1-7 | H | H | iBu | H | H | H | 3-OH | H | H |
| 1-8 | H | H | sBu | H | H | H | 3-OH | H | H |
| 1-9 | H | H | tBu | H | H | H | 3-OH | H | H |
| 1-10 | H | H | OH | H | H | H | 3-OH | H | H |
| 1-11 | H | H | OMe | H | H | H | 3-OH | H | H |
| 1-12 | H | H | OEt | H | H | H | 3-OH | H | H |
| 1-13 | H | H | OPr | H | H | H | 3-OH | H | H |
| 1-14 | H | H | OiPr | H | H | H | 3-OH | H | H |
| 1-15 | H | H | OBu | H | H | H | 3-OH | H | H |
| 1-16 | H | H | OiBu | H | H | H | 3-OH | H | H |
| 1-17 | H | H | OsBu | H | H | H | 3-OH | H | H |
| 1-18 | H | H | OtBu | H | H | H | 3-OH | H | H |
| 1-19 | H | H | SH | H | H | H | 3-OH | H | H |
| 1-20 | H | H | SMe | H | H | H | 3-OH | H | H |
| 1-21 | H | H | SEt | H | H | H | 3-OH | H | H |
| 1-22 | H | H | $NH_2$ | H | H | H | 3-OH | H | H |
| 1-23 | H | H | NHMe | H | H | H | 3-OH | H | H |
| 1-24 | H | H | $NMe_2$ | H | H | H | 3-OH | H | H |
| 1-25 | H | H | NMeEt | H | H | H | 3-OH | H | H |
| 1-26 | H | H | $NEt_2$ | H | H | H | 3-OH | H | H |
| 1-27 | H | Me | H | H | H | H | 3-OH | H | H |
| 1-28 | Me | Me | H | H | H | H | 3-OH | H | H |
| 1-29 | H | Me | Me | H | H | H | 3-OH | H | H |
| 1-30 | H | Et | Me | H | H | H | 3-OH | H | H |
| 1-31 | Me | Me | Me | H | H | H | 3-OH | H | H |
| 1-32 | H | Me | Et | H | H | H | 3-OH | H | H |
| 1-33 | H | Et | Et | H | H | H | 3-OH | H | H |
| 1-34 | Me | Me | Et | H | H | H | 3-OH | H | H |
| 1-35 | Et | Et | Et | H | H | H | 3-OH | H | H |
| 1-36 | H | Me | Pr | H | H | H | 3-OH | H | H |
| 1-37 | H | Et | Pr | H | H | H | 3-OH | H | H |
| 1-38 | Me | Me | Pr | H | H | H | 3-OH | H | H |
| 1-39 | Et | Et | Pr | H | H | H | 3-OH | H | H |
| 1-40 | H | Me | iPr | H | H | H | 3-OH | H | H |
| 1-41 | H | Et | iPr | H | H | H | 3-OH | H | H |
| 1-42 | Me | Me | iPr | H | H | H | 3-OH | H | H |
| 1-43 | Et | Et | iPr | H | H | H | 3-OH | H | H |
| 1-44 | H | Me | Bu | H | H | H | 3-OH | H | H |
| 1-45 | H | Et | Bu | H | H | H | 3-OH | H | H |
| 1-46 | Me | Me | Bu | H | H | H | 3-OH | H | H |
| 1-47 | Et | Et | Bu | H | H | H | 3-OH | H | H |
| 1-48 | H | Me | iBu | H | H | H | 3-OH | H | H |
| 1-49 | Me | Me | iBu | H | H | H | 3-OH | H | H |
| 1-50 | H | Me | sBu | H | H | H | 3-OH | H | H |
| 1-51 | Me | Me | sBu | H | H | H | 3-OH | H | H |
| 1-52 | H | Me | tBu | H | H | H | 3-OH | H | H |
| 1-53 | Me | Me | tBu | H | H | H | 3-OH | H | H |
| 1-54 | H | Me | OH | H | H | H | 3-OH | H | H |
| 1-55 | Me | Me | OH | H | H | H | 3-OH | H | H |
| 1-56 | H | Me | OMe | H | H | H | 3-OH | H | H |
| 1-57 | Me | Me | OMe | H | H | H | 3-OH | H | H |
| 1-58 | H | Me | OEt | H | H | H | 3-OH | H | H |
| 1-59 | Me | Me | OEt | H | H | H | 3-OH | H | H |
| 1-60 | H | Me | OPr | H | H | H | 3-OH | H | H |
| 1-61 | Me | Me | OPr | H | H | H | 3-OH | H | H |
| 1-62 | H | Me | OiPr | H | H | H | 3-OH | H | H |
| 1-63 | Me | Me | OiPr | H | H | H | 3-OH | H | H |
| 1-64 | H | Me | SH | H | H | H | 3-OH | H | H |
| 1-65 | H | Et | SH | H | H | H | 3-OH | H | H |

TABLE 1-continued (1)

Structure: Pyrimidine with R³ at 2-position, R⁴ at 5-position, and at 4,6-positions N(R¹)-phenyl(Z¹,Z³,Z⁴) and N(R²)-phenyl(Z²,Z⁵)-OH respectively.

| Exemplified Compound No. | R¹ | R² | R³ | R⁴ | Z¹ | Z² | Z³ | Z⁴ | Z⁵ |
|---|---|---|---|---|---|---|---|---|---|
| 1-66 | Me | Me | SH | H | H | H | 3-OH | H | H |
| 1-67 | Et | Et | SH | H | H | H | 3-OH | H | H |
| 1-68 | H | Me | SMe | H | H | H | 3-OH | H | H |
| 1-69 | H | Et | SMe | H | H | H | 3-OH | H | H |
| 1-70 | Me | Me | SMe | H | H | H | 3-OH | H | H |
| 1-71 | Et | Et | SMe | H | H | H | 3-OH | H | H |
| 1-72 | H | Me | SEt | H | H | H | 3-OH | H | H |
| 1-73 | Me | Me | SEt | H | H | H | 3-OH | H | H |
| 1-74 | H | Me | NH₂ | H | H | H | 3-OH | H | H |
| 1-75 | H | Et | NH₂ | H | H | H | 3-OH | H | H |
| 1-76 | Me | Me | NH₂ | H | H | H | 3-OH | H | H |
| 1-77 | Et | Et | NH₂ | H | H | H | 3-OH | H | H |
| 1-78 | H | Me | NHMe | H | H | H | 3-OH | H | H |
| 1-79 | Me | Me | NHMe | H | H | H | 3-OH | H | H |
| 1-80 | H | Me | NMe₂ | H | H | H | 3-OH | H | H |
| 1-81 | Me | Me | NMe₂ | H | H | H | 3-OH | H | H |
| 1-82 | H | Me | NMeEt | H | H | H | 3-OH | H | H |
| 1-83 | Me | Me | NMeEt | H | H | H | 3-OH | H | H |
| 1-84 | H | Me | NEt₂ | H | H | H | 3-OH | H | H |
| 1-85 | Me | Me | NEt₂ | H | H | H | 3-OH | H | H |
| 1-86 | H | H | H | H | 2-Me | 2-Me | 3-OH | H | H |
| 1-87 | H | H | H | H | 4-Me | 4-Me | 3-OH | H | H |
| 1-88 | H | H | H | H | 4-OMe | 4-OMe | 3-OH | H | H |
| 1-89 | H | H | Me | H | 4-Me | 4-Me | 3-OH | H | H |
| 1-90 | H | H | Me | H | 5-CF₃ | 5-CF₃ | 3-OH | H | H |
| 1-91 | H | H | Et | H | 4-Me | 4-Me | 3-OH | H | H |
| 1-92 | H | H | Pr | H | 4-Me | 4-Me | 3-OH | H | H |
| 1-93 | H | H | iPr | H | 4-Me | 4-Me | 3-OH | H | H |
| 1-94 | H | H | Bu | H | 4-Me | 4-Me | 3-OH | H | H |
| 1-95 | H | H | iBu | H | 4-Me | 4-Me | 3-OH | H | H |
| 1-96 | H | H | sBu | H | 4-Me | 4-Me | 3-OH | H | H |
| 1-97 | H | H | tBu | H | 4-Me | 4-Me | 3-OH | H | H |
| 1-98 | H | H | OH | H | 4-Me | 4-Me | 3-OH | H | H |
| 1-99 | H | H | SH | H | 4-Me | 4-Me | 3-OH | H | H |
| 1-100 | H | H | SMe | H | 4-Me | 4-Me | 3-OH | H | H |
| 1-101 | H | H | SEt | H | 4-Me | 4-Me | 3-OH | H | H |
| 1-102 | H | H | NH₂ | H | 4-Me | 4-Me | 3-OH | H | H |
| 1-103 | H | H | NHMe | H | 4-Me | 4-Me | 3-OH | H | H |
| 1-104 | H | H | NMe₂ | H | 4-Me | 4-Me | 3-OH | H | H |
| 1-105 | H | H | NMeEt | H | 4-Me | 4-Me | 3-OH | H | H |
| 1-106 | H | H | NEt₂ | H | 4-Me | 4-Me | 3-OH | H | H |
| 1-107 | H | H | H | H | H | H | 3-OMe | H | H |
| 1-108 | H | H | Me | H | H | H | 3-OMe | H | H |
| 1-109 | H | H | Et | H | H | H | 3-OMe | H | H |
| 1-110 | H | H | Pr | H | H | H | 3-OMe | H | H |
| 1-111 | H | H | iPr | H | H | H | 3-OMe | H | H |
| 1-112 | H | H | Bu | H | H | H | 3-OMe | H | H |
| 1-113 | H | H | OH | H | H | H | 3-OMe | H | H |
| 1-114 | H | H | H | H | H | H | 3-OEt | H | H |
| 1-115 | H | H | Me | H | H | H | 3-OEt | H | H |
| 1-116 | H | H | Et | H | H | H | 3-OEt | H | H |
| 1-117 | H | H | Pr | H | H | H | 3-OEt | H | H |
| 1-118 | H | H | iPr | H | H | H | 3-OEt | H | H |
| 1-119 | H | H | Bu | H | H | H | 3-OEt | H | H |
| 1-120 | H | H | H | H | H | H | 3-OPr | H | H |
| 1-121 | H | H | Me | H | H | H | 3-OPr | H | H |
| 1-122 | H | H | Et | H | H | H | 3-OPr | H | H |
| 1-123 | H | H | Pr | H | H | H | 3-OPr | H | H |
| 1-124 | H | H | iPr | H | H | H | 3-OPr | H | H |
| 1-125 | H | H | Bu | H | H | H | 3-OPr | H | H |
| 1-126 | H | H | OH | H | H | H | 3-OPr | H | H |
| 1-127 | H | H | H | H | H | H | 3-SH | H | H |
| 1-128 | H | H | Me | H | H | H | 3-SH | H | H |
| 1-129 | H | H | Et | H | H | H | 3-SH | H | H |
| 1-130 | H | H | Pr | H | H | H | 3-SH | H | H |

TABLE 1-continued (1)

$$\text{structure shown}$$

| Exemplified Compound No. | R¹ | R² | R³ | R⁴ | Z¹ | Z² | Z³ | Z⁴ | Z⁵ |
|---|---|---|---|---|---|---|---|---|---|
| 1-131 | H | H | iPr | H | H | H | 3-SH | H | H |
| 1-132 | H | H | Bu | H | H | H | 3-SH | H | H |
| 1-133 | H | H | OH | H | H | H | 3-SH | H | H |
| 1-134 | H | H | H | H | H | H | 3-SMe | H | H |
| 1-135 | H | H | Me | H | H | H | 3-SMe | H | H |
| 1-136 | H | H | Et | H | H | H | 3-SMe | H | H |
| 1-137 | H | H | Pr | H | H | H | 3-SMe | H | H |
| 1-138 | H | H | iPr | H | H | H | 3-SMe | H | H |
| 1-139 | H | H | Bu | H | H | H | 3-SMe | H | H |
| 1-140 | H | H | OH | H | H | H | 3-SMe | H | H |
| 1-141 | H | H | Et | H | H | H | 3-SEt | H | H |
| 1-142 | H | H | Pr | H | H | H | 3-SEt | H | H |
| 1-143 | H | H | OH | H | H | H | 3-SEt | H | H |
| 1-144 | H | H | Et | H | H | H | 3-SPr | H | H |
| 1-145 | H | H | Pr | H | H | H | 3-SPr | H | H |
| 1-146 | H | H | OH | H | H | H | 3-SPr | H | H |
| 1-147 | H | H | H | H | H | H | 3-NH₂ | H | H |
| 1-148 | H | H | Me | H | H | H | 3-NH₂ | H | H |
| 1-149 | H | H | Et | H | H | H | 3-NH₂ | H | H |
| 1-150 | H | H | Pr | H | H | H | 3-NH₂ | H | H |
| 1-151 | H | H | OH | H | H | H | 3-NH₂ | H | H |
| 1-152 | H | H | Et | H | H | H | 3-NHMe | H | H |
| 1-153 | H | H | Pr | H | H | H | 3-NHMe | H | H |
| 1-154 | H | H | OH | H | H | H | 3-NHMe | H | H |
| 1-155 | H | H | Et | H | H | H | 3-NHEt | H | H |
| 1-156 | H | H | Pr | H | H | H | 3-NHEt | H | H |
| 1-157 | H | H | OH | H | H | H | 3-NHEt | H | H |
| 1-158 | H | H | H | H | H | H | 3-F | H | H |
| 1-159 | H | H | H | H | H | H | 3-Cl | H | H |
| 1-160 | H | H | Me | H | H | H | 3-F | H | H |
| 1-161 | H | H | Me | H | H | H | 3-Cl | H | H |
| 1-162 | H | H | Pr | H | H | H | 3-F | H | H |
| 1-163 | H | H | Pr | H | H | H | 3-Cl | H | H |
| 1-164 | H | H | iPr | H | H | H | 3-F | H | H |
| 1-165 | H | H | iPr | H | H | H | 3-Cl | H | H |
| 1-166 | H | H | Bu | H | H | H | 3-F | H | H |
| 1-167 | H | H | Bu | H | H | H | 3-Cl | H | H |
| 1-168 | H | H | OH | H | H | H | 3-Cl | H | H |
| 1-169 | H | H | H | H | 4-F | 4-F | 3-OH | 6-F | 6-F |
| 1-170 | H | H | H | H | 4-Cl | 4-Cl | 3-OH | 6-Cl | 6-Cl |
| 1-171 | H | H | Me | H | 4-F | 4-F | 3-OH | 6-F | 6-F |
| 1-172 | H | H | Me | H | 4-Cl | 4-Cl | 3-OH | 6-Cl | 6-Cl |
| 1-173 | H | H | H | NO₂ | H | H | 3-OH | H | H |
| 1-174 | H | Me | H | NO₂ | H | H | 3-OH | H | H |
| 1-175 | H | Et | H | NO₂ | H | H | 3-OH | H | H |
| 1-176 | Me | Me | H | NO₂ | H | H | 3-OH | H | H |
| 1-177 | Et | Et | H | NO₂ | H | H | 3-OH | H | H |
| 1-178 | H | H | Me | NO₂ | H | H | 3-OH | H | H |
| 1-179 | H | H | Et | NO₂ | H | H | 3-OH | H | H |
| 1-180 | H | H | Pr | NO₂ | H | H | 3-OH | H | H |
| 1-181 | H | H | iPr | NO₂ | H | H | 3-OH | H | H |
| 1-182 | H | H | Bu | NO₂ | H | H | 3-OH | H | H |
| 1-183 | H | H | OH | NO₂ | H | H | 3-OH | H | H |
| 1-184 | H | H | OMe | NO₂ | H | H | 3-OH | H | H |
| 1-185 | H | H | OEt | NO₂ | H | H | 3-OH | H | H |
| 1-186 | H | H | OPr | NO₂ | H | H | 3-OH | H | H |
| 1-187 | H | H | OiPr | NO₂ | H | H | 3-OH | H | H |
| 1-188 | H | H | OBu | NO₂ | H | H | 3-OH | H | H - |
| 1-189 | H | H | SH | NO₂ | H | H | 3-OH | H | H |
| 1-190 | H | H | SMe | NO₂ | H | H | 3-OH | H | H |
| 1-191 | H | H | SEt | NO₂ | H | H | 3-OH | H | H |
| 1-192 | H | H | NH₂ | NO₂ | H | H | 3-OH | H | H |
| 1-193 | H | H | NHMe | NO₂ | H | H | 3-OH | H | H |
| 1-194 | H | H | NMe₂ | NO₂ | H | H | 3-OH | H | H |
| 1-195 | H | H | NMeEt | NO₂ | H | H | 3-OH | H | H |

TABLE 1-continued

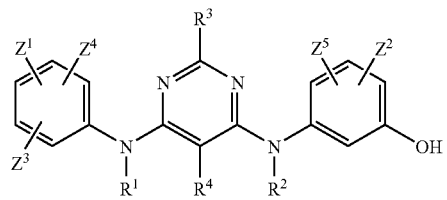

(1)

| Exemplified Compound No. | R¹ | R² | R³ | R⁴ | Z¹ | Z² | Z³ | Z⁴ | Z⁵ |
|---|---|---|---|---|---|---|---|---|---|
| 1-196 | H | H | NEt₂ | NO₂ | H | H | 3-OH | H | H |
| 1-197 | H | H | Pn | H | H | H | 3-OH | H | H |
| 1-198 | H | H | 3-MeBu | H | H | H | 3-OH | H | H |
| 1-199 | H | H | Hx | H | H | H | 3-OH | H | H |
| 1-200 | H | H | H | H | H | H | 3-NHMe | H | H |
| 1-201 | H | H | Me | H | H | H | 3-NHMe | H | H |
| 1-202 | H | H | H | H | H | H | 3-NHEt | H | H |
| 1-203 | H | H | Me | H | H | H | 3-NHEt | H | H |
| 1-204 | H | H | Et | H | H | H | 3-F | H | H |
| 1-205 | H | H | Et | H | H | H | 3-Cl | H | H |
| 1-206 | H | H | SPr | H | H | H | 3-OH | H | H |
| 1-207 | H | H | SiPr | H | H | H | 3-OH | H | H |
| 1-208 | H | Me | SPr | H | H | H | 3-OH | H | H |
| 1-209 | H | Et | SPr | H | H | H | 3-OH | H | H |
| 1-210 | Me | Me | SPr | H | H | H | 3-OH | H | H |
| 1-211 | Et | Et | SPr | H | H | H | 3-OH | H | H |
| 1-212 | H | Me | SiPr | H | H | H | 3-OH | H | H |
| 1-213 | H | Et | SiPr | H | H | H | 3-OH | H | H |
| 1-214 | Me | Me | SiPr | H | H | H | 3-OH | H | H |
| 1-215 | Et | Et | SiPr | H | H | H | 3-OH | H | H |
| 1-216 | H | H | OH | H | H | H | 3-OEt | H | H |
| 1-217 | H | H | H | H | H | H | 3-OiPr | H | H |
| 1-218 | H | H | Me | H | H | H | 3-OiPr | H | H |
| 1-219 | H | H | Et | H | H | H | 3-OiPr | H | H |
| 1-220 | H | H | Pr | H | H | H | 3-OiPr | H | H |
| 1-221 | H | H | iPr | H | H | H | 3-OiPr | H | H |
| 1-222 | H | H | Bu | H | H | H | 3-OiPr | H | H |
| 1-223 | H | H | OH | H | H | H | 3-OiPr | H | H |

TABLE 2

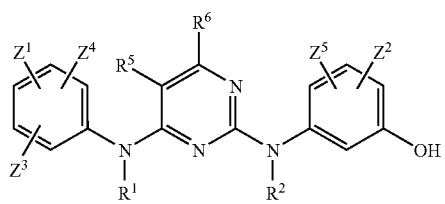

(2)

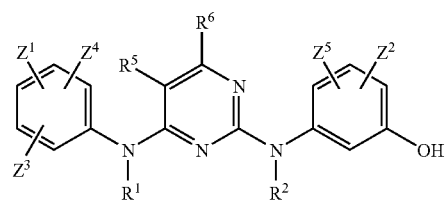

(2)

| Exemplified Compound No. | R¹ | R² | R⁵ | R⁶ | Z¹ | Z² | Z³ | Z⁴ | Z⁵ |
|---|---|---|---|---|---|---|---|---|---|
| 2-1 | H | H | H | H | H | H | 3-OH | H | H |
| 2-2 | H | Me | H | H | H | H | 3-OH | H | H |
| 2-3 | H | Et | H | H | H | H | 3-OH | H | H |
| 2-4 | Me | Me | H | H | H | H | 3-OH | H | H |
| 2-5 | Et | Et | H | H | H | H | 3-OH | H | H |
| 2-6 | H | H | H | Me | H | H | 3-OH | H | H |
| 2-7 | H | Me | H | Me | H | H | 3-OH | H | H |
| 2-8 | H | Et | H | Me | H | H | 3-OH | H | H |
| 2-9 | Me | Me | H | Me | H | H | 3-OH | H | H |
| 2-10 | Et | Et | H | Me | H | H | 3-OH | H | H |
| 2-11 | H | H | Me | Me | H | H | 3-OH | H | H |
| 2-12 | H | Me | Me | Me | H | H | 3-OH | H | H |
| 2-13 | H | Et | Me | Me | H | H | 3-OH | H | H |
| 2-14 | Me | Me | Me | Me | H | H | 3-OH | H | H |
| 2-15 | Et | Et | Me | Me | H | H | 3-OH | H | H |
| 2-16 | H | H | Me | Et | H | H | 3-OH | H | H |
| 2-17 | H | Me | Me | Et | H | H | 3-OH | H | H |
| 2-18 | H | Et | Me | Et | H | H | 3-OH | H | H |
| 2-19 | Me | Me | Me | Et | H | H | 3-OH | H | H |
| 2-20 | Et | Et | Me | Et | H | H | 3-OH | H | H |
| 2-21 | H | H | Et | Et | H | H | 3-OH | H | H |
| 2-22 | H | Me | Et | Et | H | H | 3-OH | H | H |
| 2-23 | H | Et | Et | Et | H | H | 3-OH | H | H |
| 2-24 | Me | Me | Et | Et | H | H | 3-OH | H | H |
| 2-25 | Et | Et | Et | Et | H | H | 3-OH | H | H |
| 2-26 | H | H | H | OH | H | H | 3-OH | H | H |
| 2-27 | H | Me | H | OH | H | H | 3-OH | H | H |
| 2-28 | H | Et | H | OH | H | H | 3-OH | H | H |
| 2-29 | Me | Me | H | OH | H | H | 3-OH | H | H |
| 2-30 | Et | Et | H | OH | H | H | 3-OH | H | H |
| 2-31 | H | H | H | OMe | H | H | 3-OH | H | H |
| 2-32 | H | Me | H | OMe | H | H | 3-OH | H | H |
| 2-33 | H | Et | H | OMe | H | H | 3-OH | H | H |
| 2-34 | Me | Me | H | OMe | H | H | 3-OH | H | H |
| 2-35 | Et | Et | H | OMe | H | H | 3-OH | H | H |
| 2-36 | H | H | H | OEt | H | H | 3-OH | H | H |

TABLE 2-continued

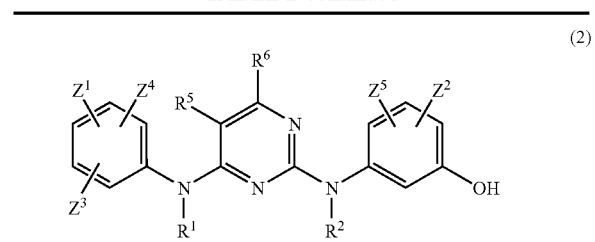

(2)

| Exemplified Compound No. | R¹ | R² | R⁵ | R⁶ | Z¹ | Z² | Z³ | Z⁴ | Z⁵ |
|---|---|---|---|---|---|---|---|---|---|
| 2-37 | H | Me | H | OEt | H | H | 3-OH | H | H |
| 2-38 | H | Et | H | OEt | H | H | 3-OH | H | H |
| 2-39 | Me | Me | H | OEt | H | H | 3-OH | H | H |
| 2-40 | Et | Et | H | OEt | H | H | 3-OH | H | H |
| 2-41 | H | H | H | OPr | H | H | 3-OH | H | H |
| 2-42 | H | Me | H | OPr | H | H | 3-OH | H | H |
| 2-43 | H | Et | H | OPr | H | H | 3-OH | H | H |
| 2-44 | Me | Me | H | OPr | H | H | 3-OH | H | H |
| 2-45 | Et | Et | H | OPr | H | H | 3-OH | H | H |
| 2-46 | H | H | H | OiPr | H | H | 3-OH | H | H |
| 2-47 | H | Me | H | OiPr | H | H | 3-OH | H | H |
| 2-48 | H | Et | H | OiPr | H | H | 3-OH | H | H |
| 2-49 | Me | Me | H | OiPr | H | H | 3-OH | H | H |
| 2-50 | Et | Et | H | OiPr | H | H | 3-OH | H | H |
| 2-51 | H | H | H | SH | H | H | 3-OH | H | H |
| 2-52 | H | Me | H | SH | H | H | 3-OH | H | H |
| 2-53 | H | Et | H | SH | H | H | 3-OH | H | H |
| 2-54 | Me | Me | H | SH | H | H | 3-OH | H | H |
| 2-55 | Et | Et | H | SH | H | H | 3-OH | H | H |
| 2-56 | H | H | H | SMe | H | H | 3-OH | H | H |
| 2-57 | H | Me | H | SMe | H | H | 3-OH | H | H |
| 2-58 | H | Et | H | SMe | H | H | 3-OH | H | H |
| 2-59 | Me | Me | H | SMe | H | H | 3-OH | H | H |
| 2-60 | Et | Et | H | SMe | H | H | 3-OH | H | H |
| 2-61 | H | H | H | SEt | H | H | 3-OH | H | H |
| 2-62 | H | Me | H | SEt | H | H | 3-OH | H | H |
| 2-63 | H | Et | H | SEt | H | H | 3-OH | H | H |
| 2-64 | Me | Me | H | SEt | H | H | 3-OH | H | H |
| 2-65 | Et | Et | H | SEt | H | H | 3-OH | H | H |
| 2-66 | H | H | H | SPr | H | H | 3-OH | H | H |
| 2-67 | H | Me | H | SPr | H | H | 3-OH | H | H |
| 2-68 | H | Et | H | SPr | H | H | 3-OH | H | H |
| 2-69 | Me | Me | H | SPr | H | H | 3-OH | H | H |
| 2-70 | Et | Et | H | SPr | H | H | 3-OH | H | H |
| 2-71 | H | H | H | SiPr | H | H | 3-OH | H | H |
| 2-72 | H | Me | H | SiPr | H | H | 3-OH | H | H |
| 2-73 | H | Et | H | SiPr | H | H | 3-OH | H | H |
| 2-74 | Me | Me | H | SiPr | H | H | 3-OH | H | H |
| 2-75 | Et | Et | H | SiPr | H | H | 3-OH | H | H |
| 2-76 | H | H | H | $NH_2$ | H | H | 3-OH | H | H |
| 2-77 | H | Me | H | $NH_2$ | H | H | 3-OH | H | H |
| 2-78 | H | Et | H | $NH_2$ | H | H | 3-OH | H | H |
| 2-79 | Me | Me | H | $NH_2$ | H | H | 3-OH | H | H |
| 2-80 | Et | Et | H | $NH_2$ | H | H | 3-OH | H | H |
| 2-81 | H | H | H | NHMe | H | H | 3-OH | H | H |
| 2-82 | H | Me | H | NHMe | H | H | 3-OH | H | H |
| 2-83 | H | Et | H | NHMe | H | H | 3-OH | H | H |
| 2-84 | Me | Me | H | NHMe | H | H | 3-OH | H | H |
| 2-85 | Et | Et | H | NHMe | H | H | 3-OH | H | H |
| 2-86 | H | H | H | $NMe_2$ | H | H | 3-OH | H | H |
| 2-87 | H | Me | H | $NMe_2$ | H | H | 3-OH | H | H |
| 2-88 | H | Et | H | $NMe_2$ | H | H | 3-OH | H | H |
| 2-89 | Me | Me | H | $NMe_2$ | H | H | 3-OH | H | H |
| 2-90 | Et | Et | H | $NMe_2$ | H | H | 3-OH | H | H |
| 2-91 | H | H | H | NMeEt | H | H | 3-OH | H | H |
| 2-92 | H | Me | H | NMeEt | H | H | 3-OH | H | H |
| 2-93 | H | Et | H | NMeEt | H | H | 3-OH | H | H |
| 2-94 | Me | Me | H | NMeEt | H | H | 3-OH | H | H |
| 2-95 | Et | Et | H | NMeEt | H | H | 3-OH | H | H |
| 2-96 | H | H | H | $NEt_2$ | H | H | 3-OH | H | H |
| 2-97 | H | Me | H | $NEt_2$ | H | H | 3-OH | H | H |
| 2-98 | H | Et | H | $NEt_2$ | H | H | 3-OH | H | H |
| 2-99 | Me | Me | H | $NEt_2$ | H | H | 3-OH | H | H |
| 2-100 | Et | Et | H | $NEt_2$ | H | H | 3-OH | H | H |
| 2-101 | H | H | H | H | 2-Me | 2-Me | 3-OH | H | H |

TABLE 2-continued

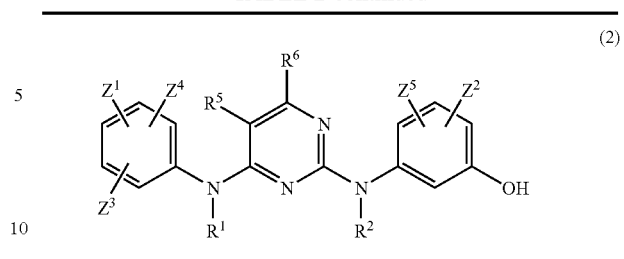

(2)

| Exemplified Compound No. | R¹ | R² | R⁵ | R⁶ | Z¹ | Z² | Z³ | Z⁴ | Z⁵ |
|---|---|---|---|---|---|---|---|---|---|
| 2-102 | H | H | H | H | 4-Me | 4-Me | 3-OH | H | H |
| 2-103 | H | H | H | Me | 4-Me | 4-Me | 3-OH | H | H |
| 2-104 | H | H | H | Et | 4-Me | 4-Me | 3-OH | H | H |
| 2-105 | H | H | Me | Me | 4-Me | 4-Me | 3-OH | H | H |
| 2-106 | H | H | Et | Et | 4-Me | 4-Me | 3-OH | H | H |
| 2-107 | H | H | H | NHEt | H | H | 3-OH | H | H |
| 2-108 | H | Me | H | NHEt | H | H | 3-OH | H | H |
| 2-109 | H | Et | H | NHEt | H | H | 3-OH | H | H |
| 2-110 | Me | Me | H | NHEt | H | H | 3-OH | H | H |
| 2-111 | Et | Et | H | NHEt | H | H | 3-OH | H | H |

TABLE 3

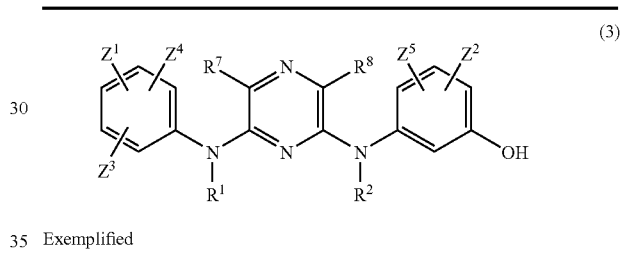

(3)

| Exemplified Compound Number | R¹ | R² | R⁷ | R⁸ | Z¹ | Z² | Z³ | Z⁴ | Z⁵ |
|---|---|---|---|---|---|---|---|---|---|
| 3-1 | H | H | H | H | H | H | 3-OH | H | H |
| 3-2 | H | Me | H | H | H | H | 3-OH | H | H |
| 3-3 | H | Et | H | H | H | H | 3-OH | H | H |
| 3-4 | Me | Me | H | H | H | H | 3-OH | H | H |
| 3-5 | Et | Et | H | H | H | H | 3-OH | H | H |
| 3-6 | H | H | Me | H | H | H | 3-OH | H | H |
| 3-7 | H | Me | Me | H | H | H | 3-OH | H | H |
| 3-8 | H | Et | Me | H | H | H | 3-OH | H | H |
| 3-9 | Me | Me | Me | H | H | H | 3-OH | H | H |
| 3-10 | Et | Et | Me | H | H | H | 3-OH | H | H |
| 3-11 | H | H | Me | Me | H | H | 3-OH | H | H |
| 3-12 | H | Me | Me | Me | H | H | 3-OH | H | H |
| 3-13 | H | Et | Me | Me | H | H | 3-OH | H | H |
| 3-14 | Me | Me | Me | Me | H | H | 3-OH | H | H |
| 3-15 | Et | Et | Me | Me | H | H | 3-OH | H | H |
| 3-16 | H | H | Me | Et | H | H | 3-OH | H | H |
| 3-17 | H | Me | Me | Et | H | H | 3-OH | H | H |
| 3-18 | H | Et | Me | Et | H | H | 3-OH | H | H |
| 3-19 | Me | Me | Me | Et | H | H | 3-OH | H | H |
| 3-20 | Et | Et | Me | Et | H | H | 3-OH | H | H |
| 3-21 | H | H | Et | Et | H | H | 3-OH | H | H |
| 3-22 | H | Me | Et | Et | H | H | 3-OH | H | H |
| 3-23 | H | Et | Et | Et | H | H | 3-OH | H | H |
| 3-24 | Me | Me | Et | Et | H | H | 3-OH | H | H |
| 3-25 | Et | Et | Et | Et | H | H | 3-OH | H | H |
| 3-26 | H | H | H | H | 4-Me | 4-Me | 3-OH | H | H |
| 3-27 | H | H | H | Me | 4-Me | 4-Me | 3-OH | H | H |
| 3-28 | H | H | Me | Me | 4-Me | 4-Me | 3-OH | H | H |
| 3-29 | H | H | Me | Me | 4-Me | 4-Me | 3-OH | H | H |
| 3-30 | H | H | Et | Et | 4-Me | 4-Me | 3-OH | H | H |
| 3-31 | H | H | H | H | 4-Et | 4-Et | 3-OH | H | H |
| 3-32 | H | H | H | Me | 4-Et | 4-Et | 3-OH | H | H |
| 3-33 | H | H | Me | Me | 4-Et | 4-Et | 3-OH | H | H |
| 3-34 | H | H | Me | Et | 4-Et | 4-Et | 3-OH | H | H |
| 3-35 | H | H | Et | Et | 4-Et | 4-Et | 3-OH | H | H |
| 3-36 | H | H | H | H | H | H | 3-OMe | H | H |

TABLE 3-continued

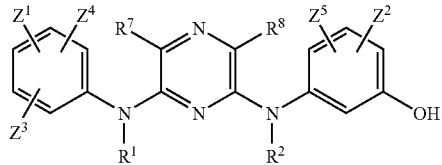
(3)

| Exemplified Compound Number | R¹ | R² | R⁷ | R⁸ | Z¹ | Z² | Z³ | Z⁴ | Z⁵ |
|---|---|---|---|---|---|---|---|---|---|
| 3-37 | H | H | H | H | H | H | 3-OEt | H | H |
| 3-38 | H | H | H | H | H | H | 3-OPr | H | H |
| 3-39 | H | H | H | H | H | H | 3-SH | H | H |
| 3-40 | H | H | H | H | H | H | 3-SMe | H | H |
| 3-41 | H | H | H | H | H | H | 3-SEt | H | H |
| 3-42 | H | H | H | H | H | H | 3-SPr | H | H |
| 3-43 | H | H | H | H | H | H | 3-NH₂ | H | H |
| 3-44 | H | H | H | H | H | H | 3-OiPr | H | H |

TABLE 4

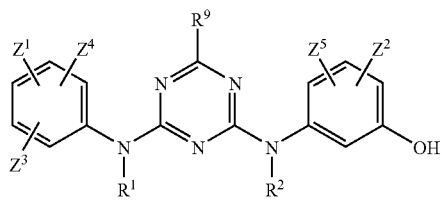
(4)

| Exemplified Compound No. | R¹ | R² | R⁹ | Z¹ | Z² | Z³ | Z⁴ | Z⁵ |
|---|---|---|---|---|---|---|---|---|
| 4-1 | H | H | Me | H | H | 3-OH | H | H |
| 4-2 | H | Me | Me | H | H | 3-OH | H | H |
| 4-3 | H | Et | Me | H | H | 3-OH | H | H |
| 4-4 | Me | Me | Me | H | H | 3-OH | H | H |
| 4-5 | Et | Et | Me | H | H | 3-OH | H | H |
| 4-6 | H | H | Et | H | H | 3-OH | H | H |
| 4-7 | H | Me | Et | H | H | 3-OH | H | H |
| 4-8 | H | Et | Et | H | H | 3-OH | H | H |
| 4-9 | Me | Me | Et | H | H | 3-OH | H | H |
| 4-10 | Et | Et | Et | H | H | 3-OH | H | H |
| 4-11 | H | H | Pr | H | H | 3-OH | H | H |
| 4-12 | H | Me | Pr | H | H | 3-OH | H | H |
| 4-13 | H | Et | Pr | H | H | 3-OH | H | H |
| 4-14 | Me | Me | Pr | H | H | 3-OH | H | H |
| 4-15 | Et | Et | Pr | H | H | 3-OH | H | H |
| 4-16 | H | H | iPr | H | H | 3-OH | H | H |
| 4-17 | H | Me | iPr | H | H | 3-OH | H | H |
| 4-18 | H | Et | iPr | H | H | 3-OH | H | H |
| 4-19 | Me | Me | iPr | H | H | 3-OH | H | H |
| 4-20 | Et | Et | iPr | H | H | 3-OH | H | H |
| 4-21 | H | H | Bu | H | H | 3-OH | H | H |
| 4-22 | H | Me | Bu | H | H | 3-OH | H | H |
| 4-23 | H | Et | Bu | H | H | 3-OH | H | H |
| 4-24 | Me | Me | Bu | H | H | 3-OH | H | H |
| 4-25 | Et | Et | Bu | H | H | 3-OH | H | H |
| 4-26 | H | H | iBu | H | H | 3-OH | H | H |
| 4-27 | H | Me | iBu | H | H | 3-OH | H | H |
| 4-28 | H | Et | iBu | H | H | 3-OH | H | H |
| 4-29 | Me | Me | iBu | H | H | 3-OH | H | H |
| 4-30 | Et | Et | iBu | H | H | 3-OH | H | H |
| 4-31 | H | H | sBu | H | H | 3-OH | H | H |
| 4-32 | H | Me | sBu | H | H | 3-OH | H | H |
| 4-33 | H | Et | sBu | H | H | 3-OH | H | H |
| 4-34 | Me | Me | sBu | H | H | 3-OH | H | H |
| 4-35 | Et | Et | sBu | H | H | 3-OH | H | H |
| 4-36 | H | H | tBu | H | H | 3-OH | H | H |
| 4-37 | H | Me | tBu | H | H | 3-OH | H | H |
| 4-38 | H | Et | tBu | H | H | 3-OH | H | H |

TABLE 4-continued

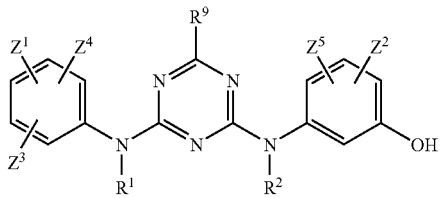
(4)

| Exemplified Compound No. | R¹ | R² | R⁹ | Z¹ | Z² | Z³ | Z⁴ | Z⁵ |
|---|---|---|---|---|---|---|---|---|
| 4-39 | Me | Me | tBu | H | H | 3-OH | H | H |
| 4-40 | Et | Et | tBu | H | H | 3-OH | H | H |
| 4-41 | H | H | Pn | H | H | 3-OH | H | H |
| 4-42 | H | Me | Pn | H | H | 3-OH | H | H |
| 4-43 | H | Et | Pn | H | H | 3-OH | H | H |
| 4-44 | Me | Me | Pn | H | H | 3-OH | H | H |
| 4-45 | Et | Et | Pn | H | H | 3-OH | H | H |
| 4-46 | H | H | 3-MeBu | H | H | 3-OH | H | H |
| 4-47 | H | Me | 3-MeBu | H | H | 3-OH | H | H |
| 4-48 | H | Et | 3-MeBu | H | H | 3-OH | H | H |
| 4-49 | Me | Me | 3-MeBu | H | H | 3-OH | H | H |
| 4-50 | Et | Et | 3-MeBu | H | H | 3-OH | H | H |
| 4-51 | H | H | Hx | H | H | 3-OH | H | H |
| 4-52 | H | Me | Hx | H | H | 3-OH | H | H |
| 4-53 | H | Et | Hx | H | H | 3-OH | H | H |
| 4-54 | Me | Me | Hx | H | H | 3-OH | H | H |
| 4-55 | Et | Et | Hx | H | H | 3-OH | H | H |
| 4-56 | H | H | OH | H | H | 3-OH | H | H |
| 4-57 | H | Me | OH | H | H | 3-OH | H | H |
| 4-58 | H | Et | OH | H | H | 3-OH | H | H |
| 4-59 | Me | Me | OH | H | H | 3-OH | H | H |
| 4-60 | Et | Et | OH | H | H | 3-OH | H | H |
| 4-61 | H | H | OMe | H | H | 3-OH | H | H |
| 4-62 | H | Me | OMe | H | H | 3-OH | H | H |
| 4-63 | H | Et | OMe | H | H | 3-OH | H | H |
| 4-64 | Me | Me | OMe | H | H | 3-OH | H | H |
| 4-65 | Et | Et | OMe | H | H | 3-OH | H | H |
| 4-66 | H | H | OEt | H | H | 3-OH | H | H |
| 4-67 | H | Me | OEt | H | H | 3-OH | H | H |
| 4-68 | H | Et | OEt | H | H | 3-OH | H | H |
| 4-69 | Me | Me | OEt | H | H | 3-OH | H | H |
| 4-70 | Et | Et | OEt | H | H | 3-OH | H | H |
| 4-71 | H | H | OPr | H | H | 3-OH | H | H |
| 4-72 | H | Me | OPr | H | H | 3-OH | H | H |
| 4-73 | H | Et | OPr | H | H | 3-OH | H | H |
| 4-74 | Me | Me | OPr | H | H | 3-OH | H | H |
| 4-75 | Et | Et | OPr | H | H | 3-OH | H | H |
| 4-76 | H | H | OiPr | H | H | 3-OH | H | H |
| 4-77 | H | Me | OiPr | H | H | 3-OH | H | H |
| 4-78 | H | Et | OiPr | H | H | 3-OH | H | H |
| 4-79 | Me | Me | OiPr | H | H | 3-OH | H | H |
| 4-80 | Et | Et | OiPr | H | H | 3-OH | H | H |
| 4-81 | H | H | OBu | H | H | 3-OH | H | H |
| 4-82 | H | Me | OBu | H | H | 3-OH | H | H |
| 4-83 | H | Et | OBu | H | H | 3-OH | H | H |
| 4-84 | Me | Me | OBu | H | H | 3-OH | H | H |
| 4-85 | Et | Et | OBu | H | H | 3-OH | H | H |
| 4-86 | H | H | OiBu | H | H | 3-OH | H | H |
| 4-87 | H | Me | OiBu | H | H | 3-OH | H | H |
| 4-88 | H | Et | OiBu | H | H | 3-OH | H | H |
| 4-89 | Me | Me | OiBu | H | H | 3-OH | H | H |
| 4-90 | Et | Et | OiBu | H | H | 3-OH | H | H |
| 4-91 | H | H | OsBu | H | H | 3-OH | H | H |
| 4-92 | H | Me | OsBu | H | H | 3-OH | H | H |
| 4-93 | H | Et | OsBu | H | H | 3-OH | H | H |
| 4-94 | Me | Me | OsBu | H | H | 3-OH | H | H |
| 4-95 | Et | Et | OsBu | H | H | 3-OH | H | H |
| 4-96 | H | H | OtBu | H | H | 3-OH | H | H |
| 4-97 | H | Me | OtBu | H | H | 3-OH | H | H |
| 4-98 | H | Et | OtBu | H | H | 3-OH | H | H |
| 4-99 | Me | Me | OtBu | H | H | 3-OH | H | H |
| 4-100 | Et | Et | OtBu | H | H | 3-OH | H | H |
| 4-101 | H | H | OPn | H | H | 3-OH | H | H |
| 4-102 | H | Me | OPn | H | H | 3-OH | H | H |
| 4-103 | H | Et | OPn | H | H | 3-OH | H | H |

TABLE 4-continued (4)

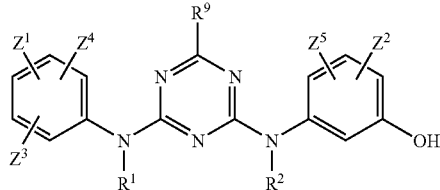

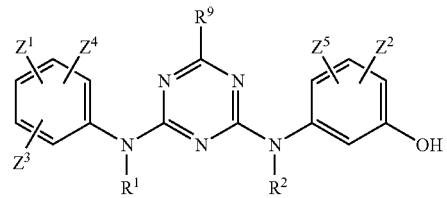

| Exemplified Compound No. | R¹ | R² | R⁹ | Z¹ | Z² | Z³ | Z⁴ | Z⁵ |
|---|---|---|---|---|---|---|---|---|
| 4-104 | Me | Me | OPn | H | H | 3-OH | H | H |
| 4-105 | Et | Et | OPn | H | H | 3-OH | H | H |
| 4-106 | H | H | O-3-MeBu | H | H | 3-OH | H | H |
| 4-107 | H | Me | O-3-MeBu | H | H | 3-OH | H | H |
| 4-108 | H | Et | O-3-MeBu | H | H | 3-OH | H | H |
| 4-109 | Me | Me | O-3-MeBu | H | H | 3-OH | H | H |
| 4-110 | Et | Et | O-3-MeBu | H | H | 3-OH | H | H |
| 4-111 | H | H | OHx | H | H | 3-OH | H | H |
| 4-112 | H | Me | OHx | H | H | 3-OH | H | H |
| 4-113 | H | Et | OHx | H | H | 3-OH | H | H |
| 4-114 | Me | Me | OHx | H | H | 3-OH | H | H |
| 4-115 | Et | Et | OHx | H | H | 3-OH | H | H |
| 4-116 | H | H | SH | H | H | 3-OH | H | H |
| 4-117 | H | Me | SH | H | H | 3-OH | H | H |
| 4-118 | H | Et | SH | H | H | 3-OH | H | H |
| 4-119 | Me | Me | SH | H | H | 3-OH | H | H |
| 4-120 | Et | Et | SH | H | H | 3-OH | H | H |
| 4-121 | H | H | SMe | H | H | 3-OH | H | H |
| 4-122 | H | Me | SMe | H | H | 3-OH | H | H |
| 4-123 | H | Et | SMe | H | H | 3-OH | H | H |
| 4-124 | Me | Me | SMe | H | H | 3-OH | H | H |
| 4-125 | Et | Et | SMe | H | H | 3-OH | H | H |
| 4-126 | H | H | SEt | H | H | 3-OH | H | H |
| 4-127 | H | Me | SEt | H | H | 3-OH | H | H |
| 4-128 | H | Et | SEt | H | H | 3-OH | H | H |
| 4-129 | Me | Me | SEt | H | H | 3-OH | H | H |
| 4-130 | Et | Et | SEt | H | H | 3-OH | H | H |
| 4-131 | H | H | SPr | H | H | 3-OH | H | H |
| 4-132 | H | Me | SPr | H | H | 3-OH | H | H |
| 4-133 | H | Et | SPr | H | H | 3-OH | H | H |
| 4-134 | Me | Me | SPr | H | H | 3-OH | H | H |
| 4-135 | Et | Et | SPr | H | H | 3-OH | H | H |
| 4-136 | H | H | SiPr | H | H | 3-OH | H | H |
| 4-137 | H | Me | SiPr | H | H | 3-OH | H | H |
| 4-138 | H | Et | SiPr | H | H | 3-OH | H | H |
| 4-139 | Me | Me | SiPr | H | H | 3-OH | H | H |
| 4-140 | Et | Et | SiPr | H | H | 3-OH | H | H |
| 4-141 | H | H | SBu | H | H | 3-OH | H | H |
| 4-142 | H | Me | SBu | H | H | 3-OH | H | H |
| 4-143 | H | Et | SBu | H | H | 3-OH | H | H |
| 4-144 | Me | Me | SBu | H | H | 3-OH | H | H |
| 4-145 | Et | Et | SBu | H | H | 3-OH | H | H |
| 4-146 | H | H | SiBu | H | H | 3-OH | H | H |
| 4-147 | H | Me | SiBu | H | H | 3-OH | H | H |
| 4-148 | H | Et | SiBu | H | H | 3-OH | H | H |
| 4-149 | Me | Me | SiBu | H | H | 3-OH | H | H |
| 4-150 | Et | Et | SiBu | H | H | 3-OH | H | H |
| 4-151 | H | H | SsBu | H | H | 3-OH | H | H |
| 4-152 | H | Me | SsBu | H | H | 3-OH | H | H |
| 4-153 | H | Et | SsBu | H | H | 3-OH | H | H |
| 4-154 | Me | Me | SsBu | H | H | 3-OH | H | H |
| 4-155 | Et | Et | SsBu | H | H | 3-OH | H | H |
| 4-156 | H | H | StBu | H | H | 3-OH | H | H |
| 4-157 | H | Me | StBu | H | H | 3-OH | H | H |
| 4-158 | H | Et | StBu | H | H | 3-OH | H | H |
| 4-159 | Me | Me | StBu | H | H | 3-OH | H | H |
| 4-160 | Et | Et | StBu | H | H | 3-OH | H | H |
| 4-161 | H | H | SPn | H | H | 3-OH | H | H |
| 4-162 | H | Me | SPn | H | H | 3-OH | H | H |
| 4-163 | H | Et | SPn | H | H | 3-OH | H | H |
| 4-164 | Me | Me | SPn | H | H | 3-OH | H | H |
| 4-165 | Et | Et | SPn | H | H | 3-OH | H | H |
| 4-166 | H | H | S-3-MeBu | H | H | 3-OH | H | H |
| 4-167 | H | Me | S-3-MeBu | H | H | 3-OH | H | H |
| 4-168 | H | Et | S-3-MeBu | H | H | 3-OH | H | H |
| 4-169 | Me | Me | S-3-MeBu | H | H | 3-OH | H | H |
| 4-170 | Et | Et | S-3-MeBu | H | H | 3-OH | H | H |
| 4-171 | H | H | SHx | H | H | 3-OH | H | H |
| 4-172 | H | Me | SHx | H | H | 3-OH | H | H |
| 4-173 | H | Et | SHx | H | H | 3-OH | H | H |
| 4-174 | Me | Me | SHx | H | H | 3-OH | H | H |
| 4-175 | Et | Et | SHx | H | H | 3-OH | H | H |
| 4-176 | H | H | NH₂ | H | H | 3-OH | H | H |
| 4-177 | H | Me | NH₂ | H | H | 3-OH | H | H |
| 4-178 | H | Et | NH₂ | H | H | 3-OH | H | H |
| 4-179 | Me | Me | NH₂ | H | H | 3-OH | H | H |
| 4-180 | Et | Et | NH₂ | H | H | 3-OH | H | H |
| 4-181 | H | H | NHMe | H | H | 3-OH | H | H |
| 4-182 | H | Me | NHMe | H | H | 3-OH | H | H |
| 4-183 | H | Et | NHMe | H | H | 3-OH | H | H |
| 4-184 | Me | Me | NHMe | H | H | 3-OH | H | H |
| 4-185 | Et | Et | NHMe | H | H | 3-OH | H | H |
| 4-186 | H | H | NMe₂ | H | H | 3-OH | H | H |
| 4-187 | H | Me | NMe₂ | H | H | 3-OH | H | H |
| 4-188 | H | Et | NMe₂ | H | H | 3-OH | H | H |
| 4-189 | Me | Me | NMe₂ | H | H | 3-OH | H | H |
| 4-190 | Et | Et | NMe₂ | H | H | 3-OH | H | H |
| 4-191 | H | H | NMeEt | H | H | 3-OH | H | H |
| 4-192 | H | Me | NMeEt | H | H | 3-OH | H | H |
| 4-193 | H | Et | NMeEt | H | H | 3-OH | H | H |
| 4-194 | Me | Me | NMeEt | H | H | 3-OH | H | H |
| 4-195 | Et | Et | NMeEt | H | H | 3-OH | H | H |
| 4-196 | H | H | NEt₂ | H | H | 3-OH | H | H |
| 4-197 | H | Me | NEt₂ | H | H | 3-OH | H | H |
| 4-198 | H | Et | NEt₂ | H | H | 3-OH | H | H |
| 4-199 | Me | Me | NEt₂ | H | H | 3-OH | H | H |
| 4-200 | Et | Et | NEt₂ | H | H | 3-OH | H | H |
| 4-201 | H | H | NEtPr | H | H | 3-OH | H | H |
| 4-202 | H | Me | NEtPr | H | H | 3-OH | H | H |
| 4-203 | H | Et | NEtPr | H | H | 3-OH | H | H |
| 4-204 | Me | Me | NEtPr | H | H | 3-OH | H | H |
| 4-205 | Et | Et | NEtPr | H | H | 3-OH | H | H |
| 4-206 | H | H | NPr₂ | H | H | 3-OH | H | H |
| 4-207 | H | Me | NPr₂ | H | H | 3-OH | H | H |
| 4-208 | H | Et | NPr₂ | H | H | 3-OH | H | H |
| 4-209 | Me | Me | NPr₂ | H | H | 3-OH | H | H |
| 4-210 | Et | Et | NPr₂ | H | H | 3-OH | H | H |
| 4-211 | H | H | Me | 4-Me | 4-Me | 3-OH | H | H |
| 4-212 | H | H | Et | 4-Me | 4-Me | 3-OH | H | H |
| 4-213 | H | H | Pr | 4-Me | 4-Me | 3-OH | H | H |
| 4-214 | H | H | iPr | 4-Me | 4-Me | 3-OH | H | H |
| 4-215 | H | H | Bu | 4-Me | 4-Me | 3-OH | H | H |
| 4-216 | H | H | iBu | 4-Me | 4-Me | 3-OH | H | H |
| 4-217 | H | H | sBu | 4-Me | 4-Me | 3-OH | H | H |
| 4-218 | H | H | tBu | 4-Me | 4-Me | 3-OH | H | H |
| 4-219 | H | H | Pn | 4-Me | 4-Me | 3-OH | H | H |
| 4-220 | H | H | 3-MeBu | 4-Me | 4-Me | 3-OH | H | H |
| 4-221 | H | H | Hx | 4-Me | 4-Me | 3-OH | H | H |
| 4-222 | H | H | OH | 4-Me | 4-Me | 3-OH | H | H |
| 4-223 | H | H | Me | H | H | 3-OMe | H | H |
| 4-224 | H | Me | Me | H | H | 3-OMe | H | H |
| 4-225 | H | Et | Me | H | H | 3-OMe | H | H |
| 4-226 | Me | Me | Me | H | H | 3-OMe | H | H |
| 4-227 | Et | Et | Me | H | H | 3-OMe | H | H |
| 4-228 | H | H | OH | H | H | 3-OMe | H | H |
| 4-229 | H | Me | OH | H | H | 3-OMe | H | H |
| 4-230 | H | Et | OH | H | H | 3-OMe | H | H |
| 4-231 | Me | Me | OH | H | H | 3-OMe | H | H |
| 4-232 | Et | Et | OH | H | H | 3-OMe | H | H |
| 4-233 | H | H | Me | H | H | 3-OEt | H | H |

TABLE 4-continued (4)

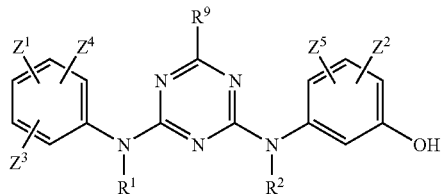
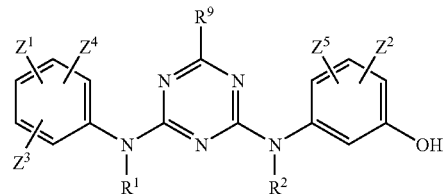

| Exemplified Compound No. | $R^1$ | $R^2$ | $R^9$ | $Z^1$ | $Z^2$ | $Z^3$ | $Z^4$ | $Z^5$ |
|---|---|---|---|---|---|---|---|---|
| 4-234 | H | Me | Me | H | H | 3-OEt | H | H |
| 4-235 | H | Et | Me | H | H | 3-OEt | H | H |
| 4-236 | Me | Me | Me | H | H | 3-OEt | H | H |
| 4-237 | Et | Et | Me | H | H | 3-OEt | H | H |
| 4-238 | H | H | OH | H | H | 3-OEt | H | H |
| 4-239 | H | Me | OH | H | H | 3-OEt | H | H |
| 4-240 | H | Et | OH | H | H | 3-OEt | H | H |
| 4-241 | Me | Me | OH | H | H | 3-OEt | H | H |
| 4-242 | Et | Et | OH | H | H | 3-OEt | H | H |
| 4-243 | H | H | Me | H | H | 3-OPr | H | H |
| 4-244 | H | Me | Me | H | H | 3-OPr | H | H |
| 4-245 | H | Et | Me | H | H | 3-OPr | H | H |
| 4-246 | Me | Me | Me | H | H | 3-OPr | H | H |
| 4-247 | Et | Et | Me | H | H | 3-OPr | H | H |
| 4-248 | H | H | OH | H | H | 3-OPr | H | H |
| 4-249 | H | Me | OH | H | H | 3-OPr | H | H |
| 4-250 | H | Et | OH | H | H | 3-OPr | H | H |
| 4-251 | Me | Me | OH | H | H | 3-OPr | H | H |
| 4-252 | Et | Et | OH | H | H | 3-OPr | H | H |
| 4-253 | H | H | Me | H | H | 3-OiPr | H | H |
| 4-254 | H | Me | Me | H | H | 3-OiPr | H | H |
| 4-255 | H | Et | Me | H | H | 3-OiPr | H | H |
| 4-256 | Me | Me | Me | H | H | 3-OiPr | H | H |
| 4-257 | Et | Et | Me | H | H | 3-OiPr | H | H |
| 4-258 | H | H | OH | H | H | 3-OiPr | H | H |
| 4-259 | H | Me | OH | H | H | 3-OiPr | H | H |
| 4-260 | H | Et | OH | H | H | 3-OiPr | H | H |
| 4-261 | Me | Me | OH | H | H | 3-OiPr | H | H |
| 4-262 | Et | Et | OH | H | H | 3-OiPr | H | H |
| 4-263 | H | H | Me | H | H | 3-SH | H | H |
| 4-264 | H | Me | Me | H | H | 3-SH | H | H |
| 4-265 | H | Et | Me | H | H | 3-SH | H | H |
| 4-266 | Me | Me | Me | H | H | 3-SH | H | H |
| 4-267 | Et | Et | Me | H | H | 3-SH | H | H |
| 4-268 | H | H | OH | H | H | 3-SH | H | H |
| 4-269 | H | Me | OH | H | H | 3-SH | H | H |
| 4-270 | H | Et | OH | H | H | 3-SH | H | H |
| 4-271 | Me | Me | OH | H | H | 3-SH | H | H |
| 4-272 | Et | Et | OH | H | H | 3-SH | H | H |
| 4-273 | H | H | Me | H | H | 3-SMe | H | H |
| 4-274 | H | Me | Me | H | H | 3-SMe | H | H |
| 4-275 | H | Et | Me | H | H | 3-SMe | H | H |
| 4-276 | Me | Me | Me | H | H | 3-SMe | H | H |
| 4-277 | Et | Et | Me | H | H | 3-SMe | H | H |
| 4-278 | H | H | OH | H | H | 3-SMe | H | H |
| 4-279 | H | Me | OH | H | H | 3-SMe | H | H |
| 4-280 | H | Et | OH | H | H | 3-SMe | H | H |
| 4-281 | Me | Me | OH | H | H | 3-SMe | H | H |
| 4-282 | Et | Et | OH | H | H | 3-SMe | H | H |
| 4-283 | H | H | Me | H | H | 3-SEt | H | H |
| 4-284 | H | Me | Me | H | H | 3-SEt | H | H |
| 4-285 | H | Et | Me | H | H | 3-SEt | H | H |
| 4-286 | Me | Me | Me | H | H | 3-SEt | H | H |
| 4-287 | Et | Et | Me | H | H | 3-SEt | H | H |
| 4-288 | H | H | OH | H | H | 3-SEt | H | H |
| 4-289 | H | Me | OH | H | H | 3-SEt | H | H |
| 4-290 | H | Et | OH | H | H | 3-SEt | H | H |
| 4-291 | Me | Me | OH | H | H | 3-SEt | H | H |
| 4-292 | Et | Et | OH | H | H | 3-SEt | H | H |
| 4-293 | H | H | Me | H | H | 3-SPr | H | H |
| 4-294 | H | Me | Me | H | H | 3-SPr | H | H |
| 4-295 | H | Et | Me | H | H | 3-SPr | H | H |
| 4-296 | Me | Me | Me | H | H | 3-SPr | H | H |
| 4-297 | Et | Et | Me | H | H | 3-SPr | H | H |
| 4-298 | H | H | OH | H | H | 3-SPr | H | H |
| 4-299 | H | Me | OH | H | H | 3-SPr | H | H |
| 4-300 | H | Et | OH | H | H | 3-SPr | H | H |
| 4-301 | Me | Me | OH | H | H | 3-SPr | H | H |
| 4-302 | Et | Et | OH | H | H | 3-SPr | H | H |
| 4-303 | H | H | Me | H | H | 3-$NH_2$ | H | H |
| 4-304 | H | Me | Me | H | H | 3-$NH_2$ | H | H |
| 4-305 | H | Et | Me | H | H | 3-$NH_2$ | H | H |
| 4-306 | Me | Me | Me | H | H | 3-$NH_2$ | H | |
| 4-307 | Et | Et | Me | H | H | 3-$NH_2$ | H | H |
| 4-308 | H | H | OH | H | H | 3-$NH_2$ | H | H |
| 4-309 | H | Me | OH | H | H | 3-$NH_2$ | H | H |
| 4-310 | H | Et | OH | H | H | 3-$NH_2$ | H | H |
| 4-311 | Me | Me | OH | H | H | 3-$NH_2$ | H | H |
| 4-312 | Et | Et | OH | H | H | 3-$NH_2$ | H | H |
| 4-313 | H | H | Me | H | H | 3-NHMe | H | H |
| 4-314 | H | Me | Me | H | H | 3-NHMe | H | H |
| 4-315 | H | Et | Me | H | H | 3-NHMe | H | H |
| 4-316 | Me | Me | Me | H | H | 3-NHMe | H | H |
| 4-317 | Et | Et | Me | H | H | 3-NHMe | H | H |
| 4-318 | H | H | OH | H | H | 3-NHMe | H | H |
| 4-319 | H | Me | OH | H | H | 3-NHMe | H | H |
| 4-320 | H | Et | OH | H | H | 3-NHMe | H | H |
| 4-321 | Me | Me | OH | H | H | 3-NHMe | H | H |
| 4-322 | Et | Et | OH | H | H | 3-NHMe | H | H |
| 4-323 | H | H | Me | H | H | 3-NHEt | H | H |
| 4-324 | H | Me | Me | H | H | 3-NHEt | H | H |
| 4-325 | H | Et | Me | H | H | 3-NHEt | H | H |
| 4-326 | Me | Me | Me | H | H | 3-NHEt | H | H |
| 4-327 | Et | Et | Me | H | H | 3-NHEt | H | H |
| 4-328 | H | H | OH | H | H | 3-NHEt | H | H |
| 4-329 | H | Me | OH | H | H | 3-NHEt | H | H |
| 4-330 | H | Et | OH | H | H | 3-NHEt | H | H |
| 4-331 | Me | Me | OH | H | H | 3-NHEt | H | H |
| 4-332 | Et | Et | OH | H | H | 3-NHEt | H | H |
| 4-333 | H | H | Me | H | H | 3-F | H | H |
| 4-334 | H | Me | Me | H | H | 3-F | H | H |
| 4-335 | H | Et | Me | H | H | 3-F | H | H |
| 4-336 | Me | Me | Me | H | H | 3-F | H | H |
| 4-337 | Et | Et | Me | H | H | 3-F | H | H |
| 4-338 | H | H | Et | H | H | 3-F | H | H |
| 4-339 | H | H | Pr | H | H | 3-F | H | H |
| 4-340 | H | H | iPr | H | H | 3-F | H | H |
| 4-341 | H | H | Bu | H | H | 3-F | H | H |
| 4-342 | H | H | OH | H | H | 3-F | H | H |
| 4-343 | H | H | Me | H | H | 3-Cl | H | H |
| 4-344 | H | Me | Me | H | H | 3-Cl | H | H |
| 4-345 | H | Et | Me | H | H | 3-Cl | H | H |
| 4-346 | Me | Me | Me | H | H | 3-Cl | H | H |
| 4-347 | Et | Et | Me | H | H | 3-Cl | H | H |
| 4-348 | H | H | Et | H | H | 3-Cl | H | H |
| 4-349 | H | H | Pr | H | H | 3-Cl | H | H |
| 4-350 | H | H | iPr | H | H | 3-Cl | H | H |
| 4-351 | H | H | Bu | H | H | 3-Cl | H | H |
| 4-352 | H | H | OH | H | H | 3-Cl | H | H |
| 4-353 | H | H | NHEt | H | H | 3-OH | H | H |
| 4-354 | H | Me | NHEt | H | H | 3-OH | H | H |
| 4-355 | H | Et | NHEt | H | H | 3-OH | H | H |
| 4-356 | Me | Me | NHEt | H | H | 3-OH | H | H |
| 4-357 | Et | Et | NHEt | H | H | 3-OH | H | H |
| 4-358 | H | H | NHPr | H | H | 3-OH | H | H |
| 4-359 | H | Me | NHPr | H | H | 3-OH | H | H |
| 4-360 | H | Et | NHPr | H | H | 3-OH | H | H |
| 4-361 | Me | Me | NHPr | H | H | 3-OH | H | H |
| 4-362 | Et | Et | NHPr | H | H | 3-OH | H | H |

TABLE 5

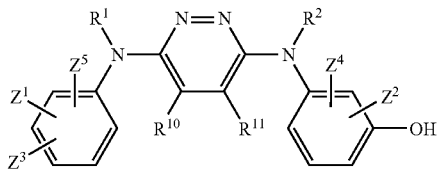

(5)

| Exemplified Compound Number | R¹ | R² | R¹⁰ | R¹¹ | Z¹ | Z² | Z³ | Z⁴ | Z⁵ |
|---|---|---|---|---|---|---|---|---|---|
| 5-1 | H | H | H | H | H | H | 3-OH | H | H |
| 5-2 | H | H | H | Me | H | H | 3-OH | H | H |
| 5-3 | H | H | H | Et | H | H | 3-OH | H | H |
| 5-4 | H | H | Me | Me | H | H | 3-OH | H | H |
| 5-5 | H | H | Et | Et | H | H | 3-OH | H | H |
| 5-6 | H | H | Pr | Pr | H | H | 3-OH | H | H |
| 5-7 | H | H | iPr | iPr | H | H | 3-OH | H | H |
| 5-8 | H | H | Bu | Bu | H | H | 3-OH | H | H |
| 5-9 | H | H | iBu | iBu | H | H | 3-OH | H | H |
| 5-10 | H | H | sBu | sBu | H | H | 3-OH | H | H |
| 5-11 | H | H | tBu | tBu | H | H | 3-OH | H | H |
| 5-12 | H | H | OMe | OMe | H | H | 3-OH | H | H |
| 5-13 | H | H | OEt | OEt | H | H | 3-OH | H | H |
| 5-14 | H | H | OPr | OPr | H | H | 3-OH | H | H |
| 5-15 | H | H | SMe | SMe | H | H | 3-OH | H | H |
| 5-16 | H | H | SEt | SEt | H | H | 3-OH | H | H |
| 5-17 | H | H | SPr | SPr | H | H | 3-OH | H | H |
| 5-18 | H | H | NH₂ | NH₂ | H | H | 3-OH | H | H |
| 5-19 | H | H | NHMe | NHMe | H | H | 3-OH | H | H |
| 5-20 | H | H | NHEt | NHEt | H | H | 3-OH | H | H |
| 5-21 | H | H | NMe₂ | NMe₂ | H | H | 3-OH | H | H |
| 5-22 | H | H | NMeEt | NMeEt | H | H | 3-OH | H | H |
| 5-23 | H | H | NEt₂ | NEt₂ | H | H | 3-OH | H | H |
| 5-24 | H | H | H | H | 4-Me | 4-Me | 3-OH | H | H |
| 5-25 | H | H | H | Me | 4-Me | 4-Me | 3-OH | H | H |
| 5-26 | H | H | H | Et | 4-Me | 4-Me | 3-OH | H | H |
| 5-27 | H | H | Me | Me | 4-Me | 4-Me | 3-OH | H | H |
| 5-28 | H | H | Et | Et | 4-Me | 4-Me | 3-OH | H | H |
| 5-29 | H | H | Pr | Pr | 4-Me | 4-Me | 3-OH | H | H |
| 5-30 | H | H | iPr | iPr | 4-Me | 4-Me | 3-OH | H | H |
| 5-31 | H | H | Bu | Bu | 4-Me | 4-Me | 3-OH | H | H |
| 5-32 | H | H | iBu | iBu | 4-Me | 4-Me | 3-OH | H | H |
| 5-33 | H | H | sBu | sBu | 4-Me | 4-Me | 3-OH | H | H |
| 5-34 | H | H | tBu | tBu | 4-Me | 4-Me | 3-OH | H | H |
| 5-35 | H | H | H | H | 4-Et | 4-Et | 3-OH | H | H |
| 5-36 | H | H | H | Me | 4-Et | 4-Et | 3-OH | H | H |
| 5-37 | H | H | H | Et | 4-Et | 4-Et | 3-OH | H | H |
| 5-38 | H | H | Me | Me | 4-Et | 4-Et | 3-OH | H | H |
| 5-39 | H | H | Et | Et | 4-Et | 4-Et | 3-OH | H | H |
| 5-40 | H | H | Pr | Pr | 4-Et | 4-Et | 3-OH | H | H |
| 5-41 | H | H | iPr | iPr | 4-Et | 4-Et | 3-OH | H | H |
| 5-42 | H | H | Bu | Bu | 4-Et | 4-Et | 3-OH | H | H |
| 5-43 | H | H | iBu | iBu | 4-Et | 4-Et | 3-OH | H | H |
| 5-44 | H | H | sBu | sBu | 4-Et | 4-Et | 3-OH | H | H |
| 5-45 | H | H | tBu | tBu | 4-Et | 4-Et | 3-OH | H | H |
| 5-46 | H | H | H | H | H | H | 3-OMe | H | H |
| 5-47 | H | H | H | Me | H | H | 3-OMe | H | H |
| 5-48 | H | H | H | H | H | H | 3-OEt | H | H |
| 5-49 | H | H | H | Me | H | H | 3-OEt | H | H |
| 5-50 | H | H | H | H | H | H | 3-OPr | H | H |
| 5-51 | H | H | H | Me | H | H | 3-OPr | H | H |
| 5-52 | H | H | H | H | H | H | 3-OiPr | H | H |
| 5-53 | H | H | H | Me | H | H | 3-OiPr | H | H |
| 5-54 | H | H | H | H | H | H | 3-SH | H | H |
| 5-55 | H | H | H | Me | H | H | 3-SH | H | H |
| 5-56 | H | H | H | H | H | H | 3-SMe | H | H |
| 5-57 | H | H | H | Me | H | H | 3-SMe | H | H |
| 5-58 | H | H | H | H | H | H | 3-SEt | H | H |
| 5-59 | H | H | H | Me | H | H | 3-SEt | H | H |
| 5-60 | H | H | H | H | H | H | 3-SPr | H | H |
| 5-61 | H | H | H | Me | H | H | 3-SPr | H | H |
| 5-62 | H | H | H | H | H | H | 3-SiPr | H | H |
| 5-63 | H | H | H | Me | H | H | 3-SiPr | H | H |
| 5-64 | H | H | H | H | H | H | 3-NH₂ | H | H |
| 5-65 | H | H | H | Me | H | H | 3-NH₂ | H | H |
| 5-66 | H | H | SiPr | SiPr | H | H | 3-OH | H | H |

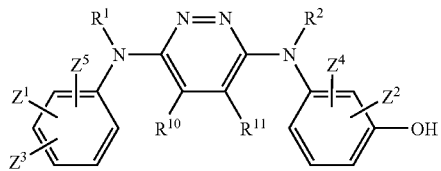

(5)

Amongst the above compounds, the preferred compounds are Exemplified Compound Nos 1-1~1-27, 1-29~1-30, 1-32, 1-36~1-37, 1-40~1-41, 1-56, 1-58, 1-60, 1-62, 1-68~1-69, 1-71~1-72, 1-74~1-75, 1-86~1-109, 1-114~1-116, 1-120~1-122, 1-127~1-136, 1-147~1-153, 1-155~1-156, 1-158~1-165, 1-173~1-175, 1-178~1-183, 1-200~1-203, 2-1~2-3, 2-6~2-8, 2-11~2-13, 2-16~2-18, 2-21~2-23, 2-31~2-33, 2-36~2-38, 2-41~2-43, 2-46~2-48, 2-56~2-58, 2-61~2-63, 2-66 ~2-68, 2-71~2-73, 2-76~2-78, 2-81~2-83, 2-86~2-88, 2-91~2-93, 2-96~2-98, 2-101~2-109, 3-1~3-3, 3-6~3-8, 3-11~3-13, 3-16~3-18, 3-21~3-23, 3-26~3-32, 4-1~4-3, 4-6~4-8, 4-11~4-13, 4-16~4-18, 4-21~4-23, 4-26~4-28, 4-31~4-33, 4-36~4-38, 4-41~4-43, 4-46~4-48, 4-51~4-53, 4-56 ~4-58, 4-61~4-63, 4-66~4-68, 4-71~4-73, 4-76~4-78, 4-81~4-83, 4-85~4-88, 4-91~4-93, 4-96~4-98, 4-101~4-103, 4-106~4-108, 4-111~4-113, 4-116~4-118, 4-121~4-123, 4-126~4-128, 4-131~4-133, 4-136~4-138, 4-141~4-143, 4-146~4-148, 4-151~4-153, 4-156~4-158, 4-161~4-163, 4-166~4-168, 4-171~4-173, 4-176~4-178, 4-181~4-183, 4-186~4-188, 4-191~4-193, 4-196~4-198, 4-201~4-203, 4-206~4-208, 4-211~4-225, 4-228~4-230, 4-233~4-235, 4-238~4-240, 2-243~4-245, 4-248~4-250, 4-253~4-255, 4-258~4-260, 4-263~4-265, 4-268~4-270, 4-273~4-275, 4-278~4-280, 4-283~4-285, 4-288~4-290, 4-303~4-305, 4-308~4-310, 4-313~4-315, 4-318~4-320, 4-323~4-325, 4-328~4-330, 4-353~4-355, 4-358~4-360, 5-1~5-7, 5-12~17, 5-24~5-29, 5-35~5-40, 5-46~5-49, 5-54~5-57, 5-64~5-65 and the following are further preferred:—

1-1~1-6, 1-11~1-12, 1-20~1-26, 1-30, 1-71, 1-87, 1-89, 1-91~1-93, 1-100~1-106, 1-127~1-131, 1-147~1-150, 1-152~1-153, 1-155~1-156, 1-161, 1-173, 1-178~1-181, 2-1, 2-6, 2-11, 2-16, 2-21, 2-31, 2-36, 2-41, 2-46, 2-56, 2-61, 2-66, 2-71, 2-76, 2-81, 2-86, 2-91, 2-96, 2-102~2-107, 3-1, 3-6, 3-11, 3-16, 3-21, 3-26~3-28, 3-31~3-32, 4-1, 4-6, 4-11, 4-16, 4-21, 4-26, 4-31, 4-36, 4-41, 4-46, 4-51, 4-56, 4-61, 4-66, 4-71, 4-76, 4-81, 4-85~4-86, 4-91, 4-96, 4-101, 4-106, 4-111, 4-116, 4-121, 4-126, 4-131, 4-136, 4-141, 4-146, 4-151, 4-156, 4-201, 4-206, 4-211~4-222, 4-263, 4-303, 4-313, 4-353, 4-358, 5-1~5-6, 5-12~5-17, 5-24~5-29, 5-35~5-39, 5-54~5-55, 5-64~5-65 with the following being still further preferred:—

1-1, 1-2, 1-3, 1-4, 1-5, 1-6, 1-22, 1-30, 1-71, 1-161, 1-173, 2-1, 2-11, 4-6, 4-11, 4-26, 4-31, 4-36, 4-81, 4-212 and 5-1 in particular, the following:—

1-1: N,N'-bis(3-hydroxyphenyl)pyrimidine-4,6-diamine 1-2: 2-methyl-N,N'-bis(3-hydroxyphenyl)pyrimidine-4,6-diamine 1-3: 2-ethyl-N,N'-bis(3-hydroxyphenyl)pyrimidine-4,6-diamine 1-4: 2-propyl-N,N'-bis(3-hydroxyphenyl)pyrimidine-4,6-diamine 1-5: 2-isopropyl-N,N'-bis(3-hydroxyphenyl)pyrimidine-4,6-diamine 1-6: 2-butyl-N,N'-bis(3-hydroxyphenyl)pyrimidine-4,6-diamine 1-22: 2-amino-N,N'-bis(3-hydroxyphenyl)pyrimidine-4,6-diamine 1-173: N,N'-bis(3-hydroxyphenyl)-5-nitropyrimidine-4,6-diamine 2-1: N,N'-bis(3-hydroxyphenyl)pyrimidine-2,4-diamine 4-6: 6-ethyl-N,N'-bis(3-hydroxyphenyl)-1,3,5-triazine-2,4-diamine 4-11: N,N'-bis(3-hydroxyphenyl)-6-propyl-1,3,5-triazine-2,4-diamine 4-26: 6-isobutyl-N,N'-bis(3-hydroxyphenyl)-1,3,5-triazine-2,4-diamine 4-31: 6-s-butyl-N,N'-bis(3-hydroxyphenyl)-1,3,5-triazine-2,4-diamine 4-36: 6-t-butyl-N,N'-bis(3-hydroxyphenyl)-1,3,5-triazine-2,4-diamine 4-212: 6-ethyl-N,N'-bis(3-hydroxy-4-methylphenyl)-1,3,5-triazine-2,4-diamine and 5-1: N,N'-bis(3-hydroxyphenyl)pyridazine-3,6-diamine, and most preferably 2-methyl-N,N'-bis(3-hydroxyphenyl)pyrimidine-4,6-diamine and N,N'-bis(3-hydroxyphenyl)pyridazine-3,6-diamine.

[Mode of Practising the Invention]

The nitrogen-containing heteroaryl compounds represented by general formulae (I) of the present invention and the nitrogen-containing heteroaryl derivatives represented by general formulae (VII) and (VIII) are either known compounds (for example WO00/12485 pamphlet) or they can be produced by the following method using known compounds as the starting materials.

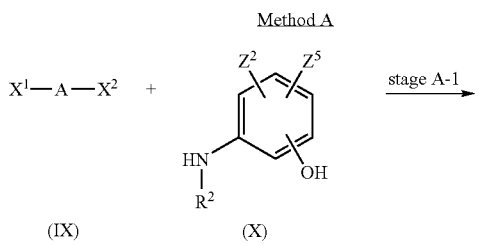

Method A

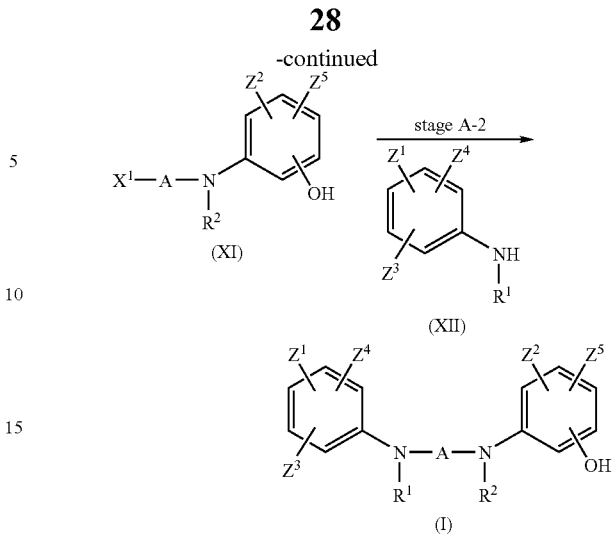

In the above formulae, $R^1$, $R^2$, $Z^1$, $Z^2$, $Z^3$, $Z^4$, $Z^5$ and A have the same meanings as above, and $X^1$ and $X^2$ each represents a halogen atom (preferably a chlorine atom, bromine atom or iodine atom, and more preferably a chlorine atom).

Stage A-1 is a stage for the production of a compound of general formula (XI) by the reaction between a halogen compound of general formula (IX) and an aminophenol of general formula (X) in an inert solvent.

The inert solvent used is not particularly restricted providing it does not impede the reaction, and to some extent dissolves the starting materials. Examples include aliphatic hydrocarbons such as hexane, heptane, ligroin and petroleum ether; aromatic hydrocarbons such as benzene, toluene and xylene; halo-hydrocarbons such as dichloromethane, chloroform, carbon tetrachloride, dichloroethane, chlorobenzene and dichlorobenzene; nitriles such as acetonitrile and propionitrile; ethers such as diethyl ether, diisopropyl ether, tetrahydrofuran, dioxane, dimethoxyethane and diethylene glycol dimethyl ether; amides such as formamide, dimethylformamide, dimethylacetamide, N-methyl-2-pyrrolidone and hexamethylphosphoramide; sulphoxides such as dimethylsulphoxide and sulfolane; and alcohols such as methanol, ethanol, propanol, 2-ethoxyethanol and 2-butoxyethanol. The ethers, amides and alcohols are preferred, in particular dioxane, diethylene glycol dimethyl ether, dimethylformamide, dimethylacetamide, 2-ethoxyethanol or 2-butoxyethanol.

This stage can be carried out with the optional addition of a base, such as an organic base like triethylamine, N-methylmorpholine, pyridine, 4-(N,N-dimethylamino)-pyridine, or an alkali metal carbonate such as sodium carbonate or potassium carbonate. An organic base is preferred.

The reaction temperature will differ with the starting material compounds and the solvent but, normally, it is 0-200° C. and preferably 50-170° C.

The reaction time will vary with the reaction temperature, the starting material compounds and the solvent but, normally, it is in the range from 10 minutes to 24 hours, and preferably 30 minutes to 8 hours.

Following the end of the reaction, the target material can be obtained from the reaction mixture by the usual methods. For example, following the end of the reaction the solvent is distilled off and water poured onto the residue obtained, then extraction performed with a water-immiscible solvent (such as benzene, ether, ethyl acetate or the like), after which the extraction liquid is washed with water and dried with anhydrous magnesium sulphate. By then distilling off the solvent, the target compound is obtained. The target compound thus obtained can, where necessary, be further purified by the usual methods, such as column chromatography, etc.

The aminophenol (X) used in stage A-1 is either a known compound or can be readily produced by known methods [see J. Am. Chem. Soc., Vol. 47, 1712-1718 (1925), J. Heterocyclic Chem., Vol. 26, 1255-1259 (1989), Synthesis, 1446-1450 (1997), J. Chem. Soc., 3017-3020 (1949), J. Chem. Soc., 2426-2430 (1951)].

Stage A-2 is a stage for the production of the target compound (I), and this is achieved by performing reaction between the compound of general formula (XI) and an amine of general formula (XII) in the same way as in stage A-1.

In the case where compound (X) and compound (XII) are the same compound, then it is possible to obtain the desired compound (I) by carrying out reaction in the same way as in stage A-1 using at least 2 mol (preferably 2-3 mol) of compound (X) per mol of halo-compound (IX).

The amine of general formula (XII) used in stage A-2 is either a known compound or is readily produced by known methods [Synth. Commun., Vol. 30, 3639-3644 (2000)].

The compound (IXa) where, in the compound of general formula (IX) employed in stage A-1, A is a group of formula (V) and $R^9$ is a $C_{1-6}$ alkyl group, can be produced by the following method B.

Method B

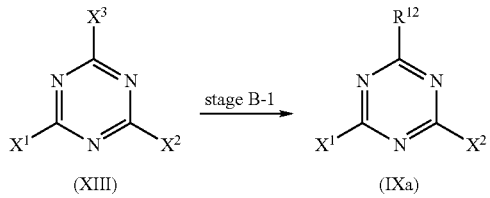

In the above formulae, $X^1$ and $X^2$ have the same meanings as above, and $X^3$ represents a halogen atom (preferably a chlorine atom, bromine atom or iodine atom, and more preferably a chlorine atom), and $R^{12}$ is a $C_{1-6}$ alkyl group.

Stage B-1 is a stage based on a known method [Helv. Chim. Acta, Vol. 33, 1365-1369 (1950)] and is carried out by the reaction between a trihalo-triazine compound of general formula (XIII) and an alkali organo-metal (for example, an organo-lithium reagent such as methyllithium, ethyllithium or propyllithium; an organo-magnesium reagent such as methylmagnesium bromide or ethyl-magnesium bromide; an organo-aluminium reagent such as trimethylaluminum; an organo-zinc reagent such as dimethylzinc; or an organo-copper reagent such as lithium dimethyl-cuprate; preferably an organo-lithium reagent or an organo-magnesium reagent) in an inert solvent (for example an aliphatic hydrocarbon such as hexane; an aromatic hydrocarbon such as benzene or toluene; a halo-hydrocarbon such as dichloromethane; or an ether such as diethyl ether or diethylene glycol dimethyl ether; preferably an aromatic hydrocarbon or an ether, and in particular benzene, toluene, tetrahydrofuran or diethyl ether), at −78° C. to 50° C. (preferably −30° C. to 30° C.) for from 10 minutes to 8 hours (preferably 30 minutes to 3 hours).

After the completion of the reaction, the target compound is obtained from the reaction mixture by the usual methods. For example, the reaction mixture is concentrated or extracted with a water-immiscible organic solvent (such as benzene, ether, ethyl acetate or the like), followed by drying with anhydrous magnesium sulphate, after which the solvent is distilled off. Where required, the target material thus obtained can be further purified by normal methods, for example by column chromatography.

The compound of general formula (IX) used in stage A-1 can also be produced by the following method C.

Method C

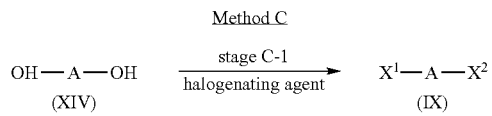

In the above formulae, $X^1$, $X^2$ and A have the same meanings as above.

Stage C-1 is a stage based on a known method [J. Org. Chem., Vol. 17, 1320-1327 (1952); J. Org. Chem., Vol. 18, 653-656 (1953); J. Am. Chem. Soc. Vol. 79, 2230-2232 (1957)] by the reaction between a compound of general formula (XIV) and a halogenating agent (such as a thionyl halide such as thionyl chloride; a phosphorus trihalide such as phosphorus trichloride, phosphorus tribromide or phosphorus triiodide; a phosphorus pentahalide such as phosphorus pentachloride, phosphorus pentabromide or phosphorus pentaiodide; or a phosphorus oxyhalide such as phosphorus oxychloride, phosphorus oxybromide or phosphorus oxyiodide; in particular with phosphorus oxychloride) either in the absence of solvent or in the presence of an inert solvent (such as an aliphatic hydrocarbon such as hexane or heptane; an aromatic hydrocarbon such as benzene or toluene; a halohydrocarbon such as dichloroethane or dichlorobenzene; an ether such as diethyl ether or diethylene glycol dimethyl ether; or an organic base such as N-methylmorpholine, triethylamine, N-methyl-piperidine, pyridine, quinoline or dimethylaniline; preferably in an organic base or in the absence of solvent, and in particular in dimethylaniline), at 20-180° C. (preferably 70-150° C.) for from 1 hour to 24 hours (preferably 3 to 5 hours). In the case where no solvent is employed, the reaction is carried out using excess of the halogenating agent.

Following the end of the reaction, the target compound is obtained from the reaction mixture by the usual methods. For example, the reaction mixture is concentrated or extracted with a water-immiscible organic solvent (such as benzene, ether, ethyl acetate or the like), followed by drying with anhydrous magnesium sulphate, after which the solvent is distilled off and the target material obtained. Where required, the target material thus obtained can be further purified by normal methods, for example by column chromatography.

In the case where the nitrogen-containing heteroaryl compounds of general formula (I) of the present invention, or pharmacologically permitted salts thereof, are used as preventives or remedies for Alzheimer's disease or as amyloid protein fibril-formation inhibitors, they can be administered orally in the form of tablets, capsules, granules, powders or syrups, etc, or parenterally in the form of injections or suppositories, etc, either on their own or after mixing with suitable pharmacologically-permitted fillers, diluents or the like.

These pharmaceutical preparations are produced by known methods using additives such as fillers/excipients (examples of which are organic fillers like lactose, sucrose, glucose, mannitol, sorbitol or other sugar or sugar derivative; corn starch, potato starch, α-starch, dextrin or other such starch or starch derivative; crystalline cellulose or other such cellulose derivative; gum Arabic; dextran; pullulan or the like; and inorganic fillers like light silica, synthetic aluminium silicate, calcium silicate, magnesium metasilicate or other silicic acid derivative; calcium hydrogen phosphate or other phosphate; calcium carbonate or other carbonate; calcium sulphate or other sulphate, or the like), lubricants (examples of which are stearic acid and metal stearates like calcium stearate and magnesium stearate; talc; colloidal silica; beeswax, sperm whale wax and other such waxes; boric acid; adipic acid; sulphates such as sodium sulphate; glycol; fumaric acid; sodium benzoate; DL-leucine; sodium laurylsulphate, magnesium laurylsulphate and other such laurylsulphates; silicic anhydride, silicic acid hydrate and other silicas; and also the aforesaid starch derivatives), binders (examples of which are hydroxypropyl cellulose, hydroxypropyl methyl cellulose, polyvinyl pyrrolidone, macrogol and compounds identical to the aforesaid fillers), disintegrating agents (cellulose derivatives such as hydroxypropyl cellulose with a low degree of substitution, carboxymethyl cellulose, calcium carboxymethyl cellulose and internally-crosslinked sodium carboxymethyl cellulose; carboxymethyl starch, sodium carboxymethyl starch, crosslinked polyvinyl pyrrolidone and other such chemically-modified starch/cellulose or the like), emulsifiers (for example bentonite, veegum and other types of colloidal clay; magnesium hydroxide, aluminium hydroxide and other such metal hydroxides; sodium lauryl sulphate, calcium stearate and other such anionic surfactants; benzalkonium chloride and other types of cationic surfactants; and polyoxyethylene alkyl ether, polyoxyethylene sorbitan fatty acid ester, sucrose fatty acid ester and other such nonionic surfactants), stabilizers (methyl paraben, propyl paraben and other such p-hydroxybenzoic acid esters; chlorobutanol, benzyl alcohol, phenyl ethyl alcohol and other such alcohols; benzalkonium chloride; phenol, cresol and other such phenols; thimerosal; dehydroacetic acid; and sorbic acid), correctives/corrigents (such as the normally used sweeteners, acidic taste-conferrers, spices and the like), diluents and other such additives.

The amount used will differ according to the symptoms, age, etc, but when administered orally to an adult there can be used an amount between a lower limit of 1 mg (preferably 10 mg) and an upper limit of 1,000 mg (preferably 500 mg) per time, and when administered intravenously there can be used an amount between a lower limit of 0.5 mg (preferably 5 mg) and an upper limit of 500 mg (preferably 250 mg) per time, from once to six times per day according to the symptoms.
[Optimum Mode for Practicing the Invention]

Below, the present invention is explained in still further detail by providing some production examples, experimental and preparation examples, but the invention is not to be restricted to these.

PRODUCTION EXAMPLE 1

6-Ethyl-N,N'-bis(3-hydroxyphenyl)-1,3,5-triazine-2,4-diamine (Exemplified Compound No. 4-6)

(1A) 2,4-dichloro-6-ethyl-1,3,5-triazine

This compound was prepared based on a known method [Helv. Chim. Acta, 33, 1365-1369 (1950)]. That is to say, 2,4,6-trichloro-1,3,5-triazine (4.61 g, 25.0 mmol) was dissolved in benzene (50.0 mL) under an atmosphere of nitrogen and the solution cooled with an ice bath.

While stirring the solution, ethylmagnesium bromide (3.0 M ether solution, 10.0 mL) was slowly added over 20 minutes and stirring carried out for a further 30 minutes while ice cooling. The reaction was monitored by thin layer chromatography and, following the end of the reaction, saturated aqueous ammonium chloride solution (20.0 mL) was added to the reaction liquid and stirring carried out. Ether (200 mL) was also added and liquid separation performed. The organic layer obtained was removed, washed with distilled water (20.0 mL) and then with saturated sodium chloride solution (20.0 mL), after which drying was carried out with anhydrous magnesium sulphate. By distilling off the solvent under reduced pressure, the crude target compound was obtained.

The crude compound thus obtained was purified using silica gel chromatography (elution solvent: hexane/ethyl acetate=100/1, v/v) and the target compound obtained (2.67 g, 60% yield).

(1B) 6-ethyl-N,N'-bis(3-hydroxyphenyl)-1,3,5-triazine-2,4-diamine

After dissolving 3-aminophenol (2.18 g, 20 mmol) in 1,4-dioxane (20.0 mL), 2,4-dichloro-6-ethyl-1,3,5-triazine (1.78 g, 10 mmol) was added and stirring carried out for 3 hours at 100° C. under a nitrogen atmosphere.

Following the end of the reaction, the solvent was distilled off under reduced pressure and the residue purified using silica gel column chromatography (elution solvent: methylene chloride/methanol=20/1, v/v) and the target compound obtained (2.26 g, yield 70%).
$^1$H NMR spectrum (DMSO, 400 MHz), δ: 1.29 (3H, t, J=7.6 Hz), 2.68 (2H, q, J=7.6 Hz), 6.59 (2H, d, J=7.2 Hz), 7.04 (2H, brs), 7.13 (2H, t, J=8.0 Hz), 7.18 (2H, d, J=7.2 Hz).
Mass spectrum (EI), m/z: 323 (M$^+$)

PRODUCTION EXAMPLE 2

2-Ethyl-N,N'-bis(3-hydroxyphenyl)pyrimidine-4,6-diamine (Exemplified Compound No. 1-3)

(2A) 4,6-dichloro-2-ethylpyrimidine

Preparation was carried out based on a known method [J. Org., Vol. 18, 653-656 (1953)]. That is to say, an excess amount of phosphoryl chloride (6.34 mL, 70.0 mmol) was added to 2-ethyl-1H-pyrimidine-4,6-dione (1.40 g, 10.0 mmol) and the reaction mixture heated under reflux for 2 hours. After the solid material had completely dissolved, the reaction mixture was cooled to room temperature, and the unreacted phosphoryl chloride distilled off under reduced pressure. The residue was added to finely crushed ice (200 g) and left. After the ice had melted, ether (200 mL) was added to the reaction mixture, and liquid separation performed. The organic layer obtained was removed, washed with distilled water (20.0 mL) and then with saturated aqueous sodium chloride solution (20.0 mL), after which drying was performed with anhydrous magnesium sulphate. By distilling off the solvent under reduced pressure, crude target compound was obtained (1.68 g, crude yield 95%).

The crude compound obtained was used in the next reaction without further purification.

(2B) 2-ethyl-N,N'-bis(3-hydroxyphenyl)pyrimidine-4,6-diamine

After dissolving 3-aminophenol (1.09 g, 10.0 mmol) in 2-ethoxyethanol (5.0 mL), 4,6-dichloro-2-ethylpyrimidine (0.89 g, 5.0 mmol) was added and stirring carried out for 5 hours at 130° C.

The reaction was monitored by thin layer chromatography and, following the end of the reaction, the solvent was distilled off under reduced pressure. The residue was purified using silica gel column chromatography (elution solvent: methylene chloride/methanol=20/1, v/v) and the target compound obtained (0.97 g, yield 60%).

$^1$H NMR spectrum (DMSO, 400 MHz), δ: 1.27 (3H, t, J=7.4 Hz), 2.62 (2H, q, J=7.4 Hz), 6.06 (1H, s), 6.37 (2H, m), 6.96 (2H, m), 7.01-7.09 (4H, m), 8.91 (2H, brs), 9.27 (2H, m).

Mass spectrum (EI), m/z: 322 (M$^+$)

PRODUCTION EXAMPLE 3

2-Methyl-N-(3-hydroxyphenyl)-N'-(3-methoxyphenyl)-pyrimidine-4,6-diamine (Exemplified Compound No. 1-108)

(3A) 2-methyl-4-chloro-6-(3-hydroxyphenylamino)-pyrimidine 4,6-dichloro-2-methylpyrimidine (1.63 g, 10.0 mmol) prepared based on the method described in Production Example 2A above using 2-methyl-1H-pyrimidine-4,6-dione instead of the 2-ethyl-1H-pyrimidine-4,6-dione, was slowly added to a 2-ethoxyethanol (5.0 mL) solution of 3-aminophenol (1.09 g, 10.0 mmol) and the reaction mixture heated for 4 hours at 130° C. The reaction was monitored by thin layer chromatography and, following the end of the reaction, the reaction mixture was cooled to room temperature and the precipitated white powder filtered off. The crude product filtered off was used in the subsequent reaction without further purification (1.76 g, crude yield 75%).

$^1$H NMR spectrum (DMSO, 400 MHz), δ: 2.42 (3H, s), 6.50 (1H, m), 6.73 (1H, s), 7.05 (1H, m), 7.12 (1H, m), 7.19 (1H, s), 10.00 (1H, s).

Mass spectrum (EI), m/z: 234 (M–H$^+$)

(3B) 2-methyl-N-(3-hydroxyphenyl)-N'-(3-methoxyphenyl)-pyrimidine-4,6-diamine 2-methyl-4-chloro-6-(3-hydroxyphenylamino)pyrimidine (0.71 g, 3.0 mmol) was added to a 2-ethoxyethanol (2.0 mL) solution of 3-methoxyaniline (0.37 g, 3.0 mmol) under a nitrogen atmosphere and the reaction mixture stirred for 5 hours at 130° C.

The reaction was monitored by thin layer chromatography and, at the end of the reaction, the solvent was distilled off under reduced pressure. The residue was purified using silica gel column chromatography (elution solvent: methylene chloride/methanol=20/1, v/v) and the target compound obtained (0.48 g, yield 50%).

$^1$H NMR spectrum (CDCl$_3$, 400 MHz), δ: 2.40 (3H, s), 3.75 (3H, s), 6.16 (1H, s), 6.59-6.74 (4H, m), 6.75 (1H, t, J=2.2 Hz), 6.83 (1H, t, J=2.2 Hz), 6.95 (2H, brs), 7.13 (1H, t, J=8.0 Hz), 7.18 (1H, t, J=8.0 Hz).

Mass spectrum (EI), m/z: 322 (M$^+$)

PRODUCTION EXAMPLE 4

2-Methyl-N,N'-bis(3-hydroxyphenyl)pyrimidine-4,6-diamine (Exemplified Compound No. 1-2)

This compound was obtained (yield 60%) based on the method described in Production Example 2B using 4,6-dichloro-2-methylpyrimidine instead of the 4,6-dichloro-2-ethylpyrimidine.

$^1$H NMR spectrum (DMSO, 400 MHz), δ: 2.35 (3H, s), 6.05 (1H, s), 6.35 (2H, m), 6.92 (2H, m), 7.00-7.10 (4H, m), 8.95 (1H, brs), 9.30 (1H, s)

Mass spectrum (EI), m/z: 308 (M$^+$).

PRODUCTION EXAMPLE 5

N,N'-bis(3-hydroxyphenyl)pyrimidine-4,6-diamine (Exemplified Compound No. 1-1)

This compound was obtained (yield 60%) based on the method described in Production Example 2B using 4,6-dichloropyrimidine instead of the 4,6-dichloro-2-ethylpyrimidine.

$^1$H NMR spectrum (DMSO, 400 MHz), δ: 6.20 (1H, s), 6.38 (2H, m), 6.92 (2H, m), 7.01-7.13 (4H, m), 8.25 (1H, s), 9.02 (1H, s), 9.31 (1H, s).

Mass spectrum (EI), m/z: 294 (M$^+$)

PRODUCTION EXAMPLE 6

N,N'-bis(3-hydroxyphenyl)pyrimidine-2,4-diamine (Exemplified Compound No. 2-1)

This compound was obtained (yield 80%) based on the method described in Production Example 2B using 2,4-dichloropyrimidine instead of the 4,6-dichloro-2-ethylpyrimidine.

$^1$H NMR spectrum (DMSO, 400 MHz), δ: 6.46 (2H, d, J=8.6 Hz), 6.63 (2H, m), 6.85 (1H, s), 6.95-7.06 (2H, m), 7.10-7.30 (3H, m), 7.93 (1H, d, J=8.2 Hz), 9.62 (1H, brs), 10.47 (1H, s), 10.80 (1H, s).

Mass spectrum (EI), m/z: 294 (M$^+$)

PRODUCTION EXAMPLE 7

5,6-Dimethyl-N,N'-bis(3-hydroxyphenyl)pyrimidine-2,4-diamine (Exemplified Compound No. 2-11)

This compound was obtained (yield 78%) based on the method described in Production Example 2B using 2,4-dichloro-5,6-dimethylpyrimidine instead of the 4,6-dichloro-2-ethylpyrimidine.

$^1$H NMR spectrum (DMSO, 400 MHz), δ: 2.12 (3H, s), 2.37 (3H, s), 6.49 (1H, dd, J=1.6, 8.2 Hz), 6.67 (2H, m), 6.88 (1H, t, J=1.6 Hz), 6.94-7.20 (2H, m), 7.06 (1H, d, J=8.2 Hz), 7.18 (1H, t, J=8.2 Hz), 9.40-9.60 (4H, brs).

Mass spectrum (EI), m/z: 322 (M$^+$)

PRODUCTION EXAMPLE 8

2-Butyl-N,N'-bis(3-hydroxyphenyl)pyrimidine-4,6-diamine (Exemplified Compound No. 1-6)

This compound was obtained (yield 73%) based on the method described in Production Example 2B using 4,6-dichloro-2-butylpyrimidine instead of the 4,6-dichloro-2-ethylpyrimidine.

$^1$H NMR spectrum (DMSO, 400 MHz), δ: 0.94 (3H, t, J=7.5 Hz), 1.38 (2H, sextet, J=7.5 Hz), 1.76 (2H, quintet, J=7.5 Hz), 2.64 (2H, t, J=7.5 Hz), 6.08 (1H, s), 6.44 (1H, dd, J=1.6, 8.0 Hz), 6.95 (2H, d, J=8.0 Hz), 7.00 (2H, m), 7.08 (2H, t, J=8.0 Hz), 9.17 (2H, s), 9.40 (2H, s)

Mass spectrum (EI), m/z: 350 (M$^+$).

PRODUCTION EXAMPLE 9

2-Propyl-N,N'-bis(3-hydroxyphenyl)pyrimidine-4,6-diamine (Exemplified Compound 1-4)

This compound was obtained (yield 68%) based on the method described in Production Example 2B using 4,6-dichloro-2-propylpyrimidine instead of the 4,6-dichloro-2-ethylpyrimidine.

$^1$H NMR spectrum (DMSO, 400 MHz), δ: 0.96 (3H, t, J=7.2 Hz), 1.79 (2H, sextet, J=7.2 Hz), 2.58 (2H, t, J=7.2 Hz), 6.06 (1H, s), 6.37 (2H, dd, J=1.2, 7.6 Hz), 6.96 (2H, d, J=8.8 Hz), 7.02-7.07 (4H, m), 8.90 (2H, s), 9.28 (22H, s).

Mass spectrum (EI), m/z: 336 (M$^+$)

PRODUCTION EXAMPLE 10

N,N'-bis(3-hydroxyphenyl)-6-propyl-1,3,5-triazine-2,4-diamine (Exemplified Compound 4-11)

This compound was obtained (yield 62%) based on the method described in Production Example 1B using 2,4-dichloro-6-propyl-1,3,5-triazine instead of the 2,4-dichloro-6-ethyl-1,3,5-triazine.

$^1$H NMR spectrum (DMSO, 400 MHz), δ: 0.96 (3H, t, J=7.2 Hz), 1.77 (2H, sextet, J=7.2 Hz), 2.51 (2H, t, J=7.2 Hz), 6.42 (2H, dd, J=2.0, 8.0 Hz), 7.05 (2H, t, J=8.0 Hz), 7.14 (2H, brs), 7.31 (2H, d, J=8.0 Hz), 9.26 (2H, brs), 9.51 (2H, brs).

Mass spectrum (EI), m/z: 337 (M$^+$)

PRODUCTION EXAMPLE 11

N-ethyl-N,N'-bis(3-hydroxyphenyl)-2-methylpyrimidine-4,6-diamine (Exemplified Compound No. 1-30)

This compound was obtained (yield 45%) based on the method described in Production Example 3B using 3-ethylaminophenol instead of the 3-methoxyaniline.

$^1$H NMR spectrum (DMSO, 400 MHz), δ: 1.06 (3H, t, J=7.3 Hz), 2.32 (3H, s), 3.87 (2H, q, J=7.3 Hz), 5.39 (1H, s), 6.25 (1H, dd, J=2.2, 8.0 Hz), 6.61 (1H, m), 6.66 (1H, d, J=8.0 Hz), 6.71 (1H, dd, J=2.2, 8.0 Hz), 6.86 (1H, d, 3=8.0 Hz), 6.92 (1H, t, J=8.0 Hz), 7.05 (1H, m), 7.25 (1H, t, J=8.0 Hz), 8.28 (1H, s), 8.68 (1H, s), 9.17 (1H, brs), 9.65 (2H, brs).

Mass spectrum (EI), m/z: 336 (M$^+$)

PRODUCTION EXAMPLE 12

N,N'-bis(3-hydroxyphenyl)pyridazine-3,6-diamine Exemplified Compound 5-1

This compound was obtained (yield 55%) based on the method described in Production Example 2B using 3,6-dichloropyridazine instead of the 4,6-dichloro-2-ethylpyrimidine.

$^1$H NMR spectrum (DMSO, 400 MHz), δ: 6.28 (2H, dd, J=2.2, 7.7 Hz), 6.96-7.07 (4H, m), 7.06 (2H, s), 7.44 (2H, t, J=2.2 Hz), 8.78 (1H, s), 9.23 (1H, s).

Mass spectrum (EI), m/z: 294 (M$^+$)

PRODUCTION EXAMPLE 13

2-Amino-N,N'-bis(3-hydroxyphenyl)pyrimidine-4,6-diamine (Exemplified Compound No. 1-22)

This compound was obtained (yield 55%) based on the method described in Production Example 2B using 2-amino-4,6-dichloropyrimidine instead of the 4,6-dichloro-2-ethylpyrimidine.

$^1$H NMR spectrum (DMSO, 400 MHz), δ: 5.49 (1H, s), 6.35 (2H, d, J=8.0 Hz), 6.75 (2H, brs), 6.77-6.86 (4H, m), 6.96 (2H, t, J=8.0 Hz), 9.14 (2H, brs), 9.36 (2H, brs).

Mass spectrum (FAB), m/z: 310 (M+H$^+$)

PRODUCTION EXAMPLE 14

2-Methylthio-N,N'-bis(3-hydroxyphenyl)pyrimidine-4,6-diamine (Exemplified Compound No. 1-20)

This compound was obtained (yield 62%) based on the method described in Production Example 2B using 4,6-dichloro-2-methylthio-pyrimidine instead of the 4,6-dichloro-2-ethylpyrimidine.

$^1$H NMR spectrum (DMSO, 400 MHz), δ: 2.48 (3H, s), 5.91 (1H, s), 6.39 (2H, dd, J=1.4, 8.0 Hz), 6.92 (2H, d, J=8.0 Hz), 6.99 (2H, m), 7.06 (2H, t, J=8.0 Hz), 9.01 (2H, s), 9.31 (2H, s), Mass spectrum (EI), m/z: 340 (M$^+$)

PRODUCTION EXAMPLE 15

2-Methylthio-N,N'-diethyl-N,N'-bis(3-hydroxyphenyl)-pyrimidine-4,6-diamine (Exemplified Compound No. 1-71)

This compound was obtained (yield 43%) based on the method described in Production Example 2B using 4,6-dichloro-2-methylthio-pyrimidine instead of the 4,6-dichloro-2-ethylpyrimidine, and using 3-ethylaminophenol instead of the 3-aminophenol.

$^1$H NMR spectrum (DMSO, 400 MHz), δ: 1.04 (6H, t, J=7.3 Hz), 2.42 (3H, s), 3.80 (4H, q, =7.3 Hz), 4.87 (1H, s), 6.50-6.60 (6H, m), 7.09 (2H, t, J=8.0 Hz), 9.42 (2H, brs).

Mass spectrum (EI), m/z: 396 (M$^+$)

PRODUCTION EXAMPLE 16

6-Butoxy-N,N'-bis(3-hydroxyphenyl)-1,3,5-triazine-2,4-diamine (Exemplified Compound No. 4-81)

This compound was obtained (yield 62%) based on the method described in Production Example 1B using 6-butoxy-2,4-dichloro-1,3,5-triazine (10.0 mmol) instead of the 2,4-dichloro-6-ethyl-1,3,5-triazine.

$^1$H NMR spectrum (DMSO, 400 MHz), δ: 0.94 (3H, t, J=7.2 Hz), 1.42 (2H, sextet, J=7.2 Hz), 1.70 (2H, quintet, J=7.2 Hz), 4.31 (2H, t, J=7.2 Hz), 6.43 (2H, dd, J=2.0, 8.0 Hz), 7.05 (2H, t, J=8.0 Hz), 7.14 (2H, brs), 7.25 (2H, brs), 9.28 (2H, brs), 9.45 (2H, brs).

Mass spectrum (FAB), m/z: 368 (M+H$^+$)

PRODUCTION EXAMPLE 17

6-Butoxy-N,N'-diethyl-N,N'-bis(3-hydroxyphenyl)-1,3,5-triazine-2,4-diamine (Exemplified Compound No. 4-85)

This compound was obtained (yield 47%) based on the method described in Production Example 1B using 6-butoxy-2,4-dichloro-1,3,5-triazine instead of the 2,4-dichloro-6-ethyl-1,3,5-triazine, and using 3-ethylaminophenol instead of the 3-aminophenol.

$^1$H NMR spectrum (DMSO, 400 MHz), δ: 0.83 (3H, t, J=7.3 Hz), 1.08 (6H, m), 1.24 (2H, m), 1.52 (2H, m), 3.79 (4H, m), 4.02 (2H, m), 6.60-6.70 (6H, m), 7.15 (2H, t, J=8.0 Hz).

Mass spectrum (FAB), m/z: 424 (M+H$^+$)

PRODUCTION EXAMPLE 18

N,N'-bis(3-hydroxyphenyl)-5-nitropyrimidine-4,6-diamine (Exemplified Compound No. 1-173)

This compound was obtained (yield 80%) based on the method described in Production Example 2B using 4,6-dichloro-5-nitropyrimidine instead of the 4,6-dichloro-2-ethylpyrimidine.
$^1$H NMR spectrum (DMSO, 400 MHz), δ: 6.65 (2H, m), 7.95 (2H, m), 7.10-7.22 (4H, m), 8.20 (1H, s), 9.60 (2H, m), 10.80 (2H, brs).
Mass spectrum (EI), m/z: 339 (M$^+$)

PRODUCTION EXAMPLE 19

N,N'-bis(3-hydroxy-2-methylphenyl)pyrimidine-4,6-diamine (Exemplified Compound No. 1-86)

This compound was obtained (yield 40%) based on the method described in Production Example 2B using 4,6-dichloropyrimidine instead of the 4,6-dichloro-2-ethylpyrimidine, and using 3-amino-2-methylphenol instead of the 3-aminophenol.
$^1$H NMR spectrum (DMSO, 400 MHz), δ: 1.95 (6H, s), 5.48 (1H, s), 6.61 (2H, d, J=5.3 Hz), 6.73 (2H, d, J=5.3 Hz), 6.92 (2H, d, J=5.3 Hz), 8.00 (1H, s), 8.29 (1H, s), 9.30 (1H, brs).
Mass spectrum (EI), m/z: 322 (M$^+$)

PRODUCTION EXAMPLE 20

N,N'-(3-hydroxy-2-methylphenyl)pyrimidine-2,4-diamine (Exemplified Compound No. 2-101)

This compound was obtained (yield 50%) based on the method described in Production Example 2B using 2,4-dichloropyrimidine (0.74 g, 5.00 mmol) instead of the 4,6-dichloro-2-ethylpyrimidine, and using 3-amino-2-methylphenol instead of the 3-aminophenol.
Mass spectrum (EI), m/z: 322 (M$^+$)

PRODUCTION EXAMPLE 21

N,N'-bis(3-hydroxy-4-methoxyphenyl)pyrimidine-4,6-diamine (Exemplified Compound No. 1-88)

This compound was obtained (yield 67%) based on the method described in Production Example 2B using 4,6-dichloropyrimidine instead of the 4,6-dichloro-2-ethylpyrimidine, and using 3-amino-4-methoxyphenol instead of the 3-aminophenol.
$^1$H NMR spectrum (DMSO, 400 MHz), δ: 3.73 (6H, s), 5.93 (1H, s), 6.81 (4H, m), 7.00 (2H, s), 8.12 (1H, s), 8.71 (1H, brs), 8.99 (1H, brs).
Mass spectrum (EI), m/z: 354 (M$^+$)

PRODUCTION EXAMPLE 22

6-Methyl-N,N'-bis(3-hydroxyphenyl)pyrimidine-2,4-diamine (Exemplified Compound 2-6)

This compound was obtained (yield 71%) based on the method described in Production Example 2B using 2,4-dichloro-6-methylpyrimidine instead of the 4,6-dichloro-2-ethylpyrimidine.
$^1$H NMR spectrum (DMSO, 400 MHz), δ: 2.36 (3H, s), 6.17 (1H, s), 6.46 (1H, dd, J=1.9, 8.5 Hz), 6.50 (1H, dd, J=1.9, 8.5 Hz), 6.94 (1H, s), 7.01-7.12 (3H, m), 7.20 (2H, t, J=8.5 Hz), 9.35 (1H, s), 9.44 (1H, s), 9.50 (1H, brs), 9.80 (1H, brs).
Mass spectrum (EI), m/z: 308 (M$^+$)

PRODUCTION EXAMPLE 23

2-Methyl-N-(3-chlorophenyl)-N'-(3-hydroxyphenyl)-pyrimidine-4,6-diamine (Exemplified Compound 1-161)

This compound was obtained (yield 57%) based on the method described in Production Example 3B using 3-chloroaniline instead of the 3-methoxyaniline.
$^1$H NMR spectrum (CDCl$_3$, 400 MHz), δ: 3.49 (3H, s), 6.10 (1H, s), 6.62 (1H, dd, J=2.0, 7.6 Hz), 6.73-6.78 (3H, m), 7.04-7.11 (2H, m), 7.17-7.25 (2H, m), 7.33 (1H, t, J=2.0 Hz).
Mass spectrum (EI), m/z: 326 (M$^+$)

PRODUCTION EXAMPLE 24

2-Methyl-N,N'-bis(4,6-difluoro-3-hydroxyphenyl)-pyrimidine-4,6-diamine (Exemplified Compound No. 1-171)

This compound was obtained (yield 57%) based on the method described in Production Example 2B using 4,6-dichloro-2-methylpyrimidine instead of the 4,6-dichloro-2-ethylpyrimidine, and using 5-amino-2,4-difluorophenol instead of the 3-aminophenol.
$^1$H NMR spectrum (DMSO, 400 MHz), δ 2.30 (3H, s), 5.77 (1H, s), 7.21 (2H, t, $^3J_{HF}$=11.0 Hz), 7.41 (2H, t, $^4J_{HF}$=8.8 Hz), 8.58 (2H, brs), 9.79 (2H, brs).
Mass spectrum (EI), m/z: 380 (M$^+$)

PRODUCTION EXAMPLE 25

2-Isopropyl-N,N'-bis(3-hydroxyphenyl)pyrimidine-4,6-diamine (Exemplified Compound No. 1-5)

This compound was obtained (yield 65%) based on the method described in Production Example 2B using 4,6-dichloro-2-isopropylpyrimidine instead of the 4,6-dichloro-2-ethylpyrimidine.
$^1$H NMR spectrum (CD$_3$OD, 400 MHz), δ: 1.32 (6H, d, J=6.9 Hz), 2.88 (1H, septet, J=6.9 Hz), 6.08 (1H, s), 6.47 (2H, ddd, J=0.9, 2.2, 8.1 Hz), 6.90 (2H, ddd, J=0.9, 2.2, 8.1 Hz), 6.98 (2H, t, J=2.2 Hz), 7.09 (2H, t, J=8.1 Hz).
Mass spectrum (EI), m/z: 336 (M$^+$)

PRODUCTION EXAMPLE 26

2-Methyl-N,N'-bis(3-hydroxy-5-trifluoromethylphenyl)-pyrimidine-4,6-diamine (Exemplified Compound No. 1-90)

This compound was obtained (yield 43%) based on the method described in Production Example 2B using 4,6-dichloro-2-methylpyrimidine instead of the 4,6-dichloro-2-ethylpyrimidine, and using 3-amino-5-trifluoromethyl-phenol instead of the 3-aminophenol.
$^1$H NMR spectrum (CD$_3$OD, 400 MHz), δ: 2.46 (3H, s), 6.05 (1H, s), 6.68 (2H, m), 7.30 (2H, m), 7.34 (2H, t, J=2.0 Hz).
Mass spectrum (EI), m/z: 444 (M$^+$)

PRODUCTION EXAMPLE 27

N,N'-bis(3-hydroxyphenyl)-6-methyl-1,3,5-triazine-2,4-diamine (Exemplified Compound No. 4-1)

This compound was obtained (yield 73%) based on the method described in Production Example 1B using 2,4-dichloro-6-methyl-1,3,5-triazine instead of the 2,4-dichloro-6-ethyl-1,3,5-triazine.
$^1$H NMR spectrum (DMSO, 400 MHz), δ: 2.29 (3H, s), 6.43 (2H, dd, J=2.4, 8.0 Hz), 7.06 (2H, t, J=8.0 Hz), 7.13 (2H, brs), 7.30 (2H, d, J=8.0 Hz), 9.27 (2H, brs), 9.53 (2H, brs).
Mass spectrum (EI), m/z: 309 (M$^+$)

PRODUCTION EXAMPLE 28

6-Butyl-N,N'-bis(3-hydroxyphenyl)-1,3,5-triazine-2,4-diamine (Exemplified Compound No. 4-21)

This compound was obtained (yield 68%) based on the method described in Production Example 1B using 6-butyl-2,4-dichloro-1,3,5-triazine instead of the 2,4-dichloro-6-ethyl-1,3,5-triazine.
$^1$H NMR spectrum (DMSO, 400 MHz), δ: 0.92 (3H, t, J=7.3 Hz), 1.37 (2H, sextet, J=7/3 Hz), 1.73 (2H, quintet, J=8.0 Hz), 2.51 (2H, m), 6.42 (2H, dd, J=2.5, 8.0 Hz), 7.05 (2H, t, J=8.0 Hz), 7.13 (2H, s), 7.31 (2H, d, J=8.0 Hz), 9.26 (2H, brs), 9.51 (2H, brs).
Mass spectrum (EI), m/z: 351 (M$^+$)

PRODUCTION EXAMPLE 29

N,N'-dimethyl-N,N'-bis(3-hydroxyphenyl)pyrimidine-4,6-diamine (Exemplified Compound No. 1-28)

This compound was obtained (yield 43%) based on the method described in Production Example 2B using 4,6-dichloropyrimidine instead of the 4,6-dichloro-2-ethylpyrimidine, and using 3-methylaminophenol instead of the 3-aminophenol.
$^1$H NMR spectrum (DMSO, 400 MHz), δ: 3.28 (6H, s), 5.50 (1H, s), 6.54-6.64 (6H, m), 7.11 (2H, t, J=8.0 Hz), 8.21 (1H, s), 9.50 (2H, brs).
Mass spectrum (EI), m/z: 340 (M$^+$)

PRODUCTION EXAMPLE 30

2-Methyl-N,N'-dimethyl-N,N'-bis(3-hydroxyphenyl)-pyrimidine-4,6-diamine (Exemplified Compound No. 1-31)

This compound was obtained (yield 45%) based on the method described in Production Example 2B using 4,6-dichloro-2-methylpyrimidine instead of the 4,6-dichloro-2-ethylpyrimidine, and using 3-methylaminophenol instead of the 3-aminophenol.
$^1$H NMR spectrum (DMSO, 400 MHz), δ: 2.31 (3H, s), 3.28 (6H, s), 5.35 (1H, s), 6.53-6.61 (6H, m), 7.09 (2H, t, J=8.0 Hz), 9.48 (2H, brs).
Mass spectrum (EI), m/z: 336 (M$^+$)

PRODUCTION EXAMPLE 31

6-Isobutyl-N,N'-bis(3-hydroxyphenyl)-1,3,5-triazine-2,4-diamine (Exemplified Compound No. 4-26)

This compound was obtained (yield 50%) based on the method described in Production Example 1B using 6-isobutyl-2,4-dichloro-1,3,5-triazine instead of the 2,4-dichloro-6-ethyl-1,3,5-triazine.
$^1$H NMR spectrum (DMSO, 400 MHz), δ: 0.99 (6H, d, J=6.8 Hz), 2.42 (1H, m), 2.49 (2H, d, J=7.2 Hz), 6.54 (2H, dd, J=1.5, 8.0 Hz), 7.00-7.09 (2H, m), 7.11 (2H, t, J=8.0 Hz), 7.21 (2H, m).
Mass spectrum (EI), m/z: 351 (M$^+$)

PRODUCTION EXAMPLE 32

6-Ethyl-N,N'-bis(3-hydroxy-4-methylphenyl)-1,3,5-triazine-2,4-diamine (Exemplified Compound No. 4-212)

This compound was obtained (yield 55%) based on the method described in Production Example 1B using 3-amino-3-methylphenol {sic} instead of the 3-aminophenol.
$^1$H NMR spectrum (DMSO, 400 MHz), δ: 1.13 (3H, t, J=7.2 Hz), 1.96 (6H, s), 2.51 (2H, q, J=7.2 Hz), 6.87 (2H, d, J=8.0 Hz), 6.98 (2H, brs), 7.02 (2H, d, J=8.0 Hz).
Mass spectrum (EI), m/z: 351 (M$^+$)

PRODUCTION EXAMPLE 33

6-t-Butyl-N,N'-bis(3-hydroxyphenyl)-1,3,5-triazine-2,4-diamine (Exemplified Compound No. 4-36)

This compound was obtained (yield 48%) based on the method described in Production Example 1B using 6-t-butyl-2,4-dichloro-1,3,5-triazine instead of the 2,4-dichloro-6-ethyl-1,3,5-triazine.
$^1$H NMR spectrum (DMSO, 400 MHz), δ: 1.32 (9H, s), 6.43 (2H, dd, J=2.0, 8.0 Hz), 7.06 (2H, t, J=8.0 Hz), 7.20 (2H, brs), 7.34 (2H, d, J=8.0 Hz), 9.27 (2H, brs), 9.39 (2H, brs).
Mass spectrum (EI), m/z: 351 (M$^+$)

PRODUCTION EXAMPLE 34

6-s-Butyl-N,N'-bis(3-hydroxyphenyl)-1,3,5-triazine-2,4-diamine (Exemplified Compound No. 4-31)

This compound was obtained (yield 52%) based on the method described in Production Example 1B using 6-s-butyl-2,4-dichloro-1,3,5-triazine instead of the 2,4-dichloro-6-ethyl-1,3,5-triazine.
$^1$H NMR spectrum (DMSO, 400 MHz), δ: 0.90 (3H, t, J=7.4 Hz), 1.26 (3H, d, J=6.4 Hz), 1.59 (1H, ddq, J=6.4, 7.4, 14.0 Hz), 1.83 (1H, ddq, J=6.4, 7.4, 14.0 Hz), 2.60 (1H, ddq, J=6.4, 6.4, 6.4 Hz), 4.00 (2H, brs), 6.51 (2H, d, J=7.2 Hz), 7.09 (2H, d, J=7.5 Hz), 7.12 (2H, s), 7.27 (2H, d, J=7.5 Hz), 9.40 (1H, brs), 9.90 (1H, brs).
Mass spectrum (EI), m/z: 351 (M$^+$)

EXAMPLE 1

Action in Inhibiting the Lowering of MTT Reduction Capacity

The HeLa cells employed were purchased from the Dainippon Pharmaceutical Co.
The HeLa cells were seeded by suspension in MEM (Minimum essential medium; produced by the Sigma Chemical Co.) containing 10% inactivated FBS (foetal bovine serum) such that there were 1,000 per well in a 96-well microplate, and then culturing was carried out overnight in an incubator at 37° C. in the presence of 5% $CO_2$.
The test compound was dissolved in dimethyl sulphoxide (DMSO) and diluted with the MEM medium so that the final concentration of DMSO was no more than 0.1 wt %, and added to the cells seeded the previous day. A solution of β-amyloid protein (Aβ1-40: produced by the Sigma Chemical Co.) dissolved in MEM medium was added so the final Aβ1-40 concentration was 100 ng/mL. Overnight culturing was carried out using an incubator at 37° C. in the presence of 5% $CO_2$, with 100 μL/well of MEM medium containing 5% deactivated FBS.

Now, prior to use, the Aβ1-40 had been dissolved in buffer and left overnight so that the amyloid coagulated.

In order to determine the percentage inhibition of the test compound, cells alone, cells where Aβ1-40 had been added, and cells where only the test compound had been added, were also incubated overnight under the same conditions.

The following day, there was added 10 μL/well of MTT [3-(4,5-dimethylthiazol-2-yl)-2,5-diphenyltetrazolium bromide: produced by Wako Pure Chemical Industries] prepared at a concentration of 5 mg/mL with phosphate buffered saline (PBS), and incubation carried out for 2 hours at 37° C. in the presence of 5% $CO_2$. The medium was then eliminated and the formazan dye produced measured calorimetrically (A570 nm-A650 nm) using a Microplate Reader (produced by the Molecular Devices Co.), by dissolving with the addition of 100 μL per well of isopropanol. In this way, the change in the MTT reduction capacity of the HeLa cells was measured.

The percentage inhibition (%) by the test compound was determined from the following formula.

$$\text{inhibition (\%)} [(a-b)/(a-c)] \times 100$$

where
a=MTT reduction capacity when untreated
b=MTT reduction capacity when Aβ1-40 and the test compound are added
c=MTT reduction capacity when only Aβ1-40 is added Table 6 shows the action in inhibiting the lowering of the MTT reduction capacity by Aβ1-40 (100 nM) in HeLa cells, denoted by the 50% inhibitory concentration (IC50).

As can seen from Table 6, the compounds of the present invention show outstanding action in inhibiting a lowering of the MTT reduction capacity.

TABLE 6

| Test Compound | IC50 (μm) |
|---|---|
| compound of Production Example 1 | 3.5 |
| compound of Production Example 2 | 1.9 |
| compound of Production Example 4 | 6.0 |
| compound of Production Example 5 | 9.6 |
| compound of Production Example 6 | 6.7 |
| compound of Production Example 8 | 5.5 |
| compound of Production Example 9 | 2.4 |
| compound of Production Example 10 | 4.2 |
| compound of Production Example 13 | 5.5 |
| compound of Production Example 18 | 3.8 |
| compound of Production Example 27 | 2.4 |
| compound of Production Example 33 | 2.2 |
| compound of Production Example 34 | 4.1 |
| compound of Production Example 35 | 2.1 |
| compound of Production Example 36 | 5.8 |

When testing was carried out by the same method as above using 4-(7-hydroxy-2,4,4-trimethyl-chroman-4-yl)benzene-1,3-diol, and the action in suppressing the lowering of MTT function measured as the 50% inhibitory concentration (IC50), the measured result obtained was 12 μM.

EXAMPLE 2

Action in Suppressing Long-Term Potentiation Inhibition

The method for testing the suppression of the impairment of long-term potentiation was based on that described in J. Neurosci. Vol. 20, 2003-10 (2000). That is to say, acute sections of thickness 400 μm were prepared from the hippocampus of the brains of 3-4 week old male Wistar rats. These acute sections were immersed in artificial cerebrospinal fluid in which β-amyloid protein (Aβ1-42: produced by the Sigma Chemical Co.) and compound from Production Examples 1 or 12 had been dissolved, and pretreatment carried out for 5 hours.

In the measurement using the compound from Production Example 1, the concentration of the Aβ1-42 in the artificial cerebrospinal fluid was 500 nM and the concentration of the compound from Production Example 1 was 1 μg/mL. In the measurement using the compound from Production Example 12, the concentration of the Aβ1-42 in the artificial cerebrospinal fluid was 1 μM and the concentration of the compound from Production Example 12 was 3 μg/mL. Now, the Aβ1-42 was used after coagulation of the amyloid by leaving overnight.

100 pulses of high frequency stimulation at 100 Hz were applied to the pretreated acute sections, and the field excitatory postsynaptic potential: fEPSP) measured by an extracellular recording method.

The fEPSP was measured at 30 second intervals following application of the high frequency stimulation and the fEPSP slope (units [%]) measured. The average values of the slope over 0-20 minutes, 20-40 minutes and 40-60 minutes were determined. This test was repeated five times over. The results are shown in Table 7. In the table, the figures are the average values ±standard deviation for the five averages obtained in the five tests. "Test 1" shows the measurements employing the compound from Production Example 1 and "Test 2" shows the measurements employing the compound from Production Example 12. "Aβ" denotes the Aβ1-42.

As controls, measurements were made of the fEPSP [mV] under the same conditions for acute sections pretreated with the artificial cerebrospinal fluid alone, acute sections pretreated with the artificial cerebrospinal fluid in which Aβ1-42 had been dissolved, and acute sections pretreated with artificial cerebrospinal fluid in which only the compound from Production Example 1 or 12 had been dissolved, and then the average value of the fEPSP slope [%] obtained.

TABLE 7

| | Value of fEPSP Slope [%] | | |
|---|---|---|---|
| | 0-20 minutes | 20-40 minutes | 40-60 minutes |
| Test 1 | | | |
| Control group | 158.8 ± 5.2 | 157.5 ± 4.2 | 155.6 ± 5.4 |
| Aβ (500 nM) | 145.8 ± 5.8 | 136.1 ± 4.0 | 113.0 ± 2.6 |
| Prod. Ex. 1 compound* (1 μg/mL) | 155.3 ± 3.4 | 156.5 ± 3.9 | 155.8 ± 5.0 |
| Aβ (500 nM) + Prod. Ex. 1 compound (1 μg/mL) | 150.0 ± 8.4 | 149.6 ± 6.9 | 151.2 ± 7.5 |
| Test 2 | | | |
| Control group | 145.8 ± 5.8 | 136.1 ± 4.0 | 113.0 ± 2.6 |
| Aβ (1 μM) | 132.3 ± 8.8 | 114.4 ± 6.4 | 103.7 ± 5.4 |
| Prod. Ex. 12 compound** (3 μg/mL) | 175.3 ± 7.4 | 162.9 ± 9.8 | 160.8 ± 10.3 |
| Aβ (1 μM) + Prod. Ex. 12 compound (3 μg/mL) | 161.7 ± 2.6 | 148.1 ± 3.1 | 146.2 ± 4.6 |

Notes:
*Prod. Ex. 1 compound = compound from Production Example 1
**Prod. Ex. 12 compound = compound from Production Example 12

In the control group, by applying high frequency stimulation, an increase in the synapse transmission was confirmed over a 60 minute period. However, in the group where the sections had been pretreated for 5 hours with Aβ1-42, while long-term potentiation was induced its maintenance was impaired.

In contrast, by pretreating for 5 hours with Aβ1-42 together with the compound synthesized in Production Example 1 or in Production Example 12, which is inactive on its own, the impairment of the LTP due to the Aβ1-42 was suppressed.

As can be seen in Table 7, the compounds of the present invention show an outstanding suppression action against the impairment of synapse transmission produced by Aβ.

Average values of the fEPSP slope [%] were determined in the same way as in the test method described above, for 4-(7-hydroxy-2,4,4-trimethyl-chroman-4-yl)benzene-1,3-diol (Compound A in the table). The measured values obtained are shown below.

TABLE 8

| | Value of fEPSP Slope [%] | | |
|---|---|---|---|
| | 0-20 minutes | 20-40 minutes | 40-60 minutes |
| Control group | 158.7 ± 5.1 | 157.5 ± 4.1 | 155.5 ± 5.3 |
| Aβ (1 μM) | 133.5 ± 9.5 | 123.8 ± 6.6 | 122.8 ± 7.1 |
| Compound A (1 μg/mL) | 168.6 ± 13.0 | 146.6 ± 15.9 | 149.7 ± 16.1 |
| Aβ (1 μM) + Compound A (1 μg/mL) | 159.5 ± 6.6 | 142.8 ± 5.4 | 137.3 ± 4.5 |

EXAMPLE 3

Aβ Fibril-Formation Inhibiting Action and Fibrillar Aβ Breakdown Action

The Aβ fibril-formation inhibiting action and fibrillar Aβ breakdown action were evaluated using the thioflavin binding assay method. The details of the test method are based on the method described in J. Biol. Chem. Vol. 274, 25945-25952 (1999).

In the measurement of the inhibition of Aβ fibril-formation, the concentration of the Aβ1-42 was 25 μM and the concentration of the compound synthesized in Production Example 4 or Production Example 12 was 100 μg/mL in each case. The measurement of the Aβ fibril-formation inhibiting action was carried out following incubation for 2 days at 37° C. of the Aβ1-42 alone and of the Aβ1-42 to which the compound synthesized in Production Example 4 or Production Example 12 had been added.

In the measurement of the fibrillar Aβ breakdown action, the concentration of the Aβ1-42 was 25 μM and the concentration of the compound synthesized in Production Example 4 or Production Example 12 was 100 μg/mL in each case. After incubating the Aβ1-42 for 2 days or 3 days at 37° C., the compound synthesized in Production Example 4 or Production Example 12 was or was not added, and then further incubation performed for 2 days, after which measurement of the fibrillar Aβ breakdown action was performed.

The measurements of the Aβ fibril-formation inhibiting action and of the fibrillar Aβ breakdown action were carried out by placing a 100 μL sample obtained by pretreatment as described above, plus 800 μL of distilled water, 1 mL of glycine (100 mM) and 50 μL of thioflavin (100 μM) in a cuvette, and measuring the fluorescence at an excitation wavelength of 435 nm and a fluorescence wavelength of 490 nm.

The results are shown in Table 9. The figures in the table show the calculated percentages taking the fluorescent intensity obtained when the fluorescence of the sample obtained by incubating Aβ1-42 (25 μM) alone by the above method, and measured at an excitation wavelength of 435 nm and a fluorescence wavelength of 490 nm, was taken as 100. The figures are in the form of the average value ±standard deviation, for the three to nine averages obtained in three to nine tests. In the table, "Test 3" shows the measurements using the compound from Production Example 4, and "Test 4" shows the measurements using the compound from Production Example 12. "Aβ" is for the Aβ1-42.

TABLE 9

| | fibril-formation inhibiting action (fluorescent intensity %) | fibrillar breakdown action (fluorescent intensity %) |
|---|---|---|
| Test 3 | | |
| Aβ (25 μM) | 100.00 ± 1.18 | 100.00 ± 8.88 |
| Aβ (25 μM) + Prod. Ex. 4 compound* (100 μg/mL) | 16.26 ± 5.30 | 30.63 ± 1.26 |
| Test 4 | | |
| Aβ (25 μM) | 100.00 ± 2.24 | 100.00 ± 2.07 |
| Aβ (25 μM) + Prod. Ex. 12 compound** (100 μg/mL) | 1.69 ± 1.324 | 28.49 ± 5.17 |

Notes:
*Prod. Ex. 4 compound = compound from Production Example 4
**Prod. Ex. 12 compound = compound from Production Example 12

With Aβ by itself, strong thioflavin fluorescence was confirmed. This shows that Aβ forms fibrils. However, in the samples obtained by adding the compound from Production Example 4 or from Production Example 12 prior to fibril formation, there was a weakening of the thioflavin fluorescence, indicating that the Aβ fibril-formation was inhibited. The same results were also obtained with samples obtained by adding the compound from Production Example 4 or Production Example 12 after fibril formation, indicating that there was a fibrillar Aβ breakdown action.

As shown in Table 8 {sic}, as well as the compounds of the present invention acting to inhibit Aβ fibril-formation, it is clear that they also act to break down formed Aβ fibrils.

PREPARATION EXAMPLE 1

A Powder Preparation Comprising the Compound from Production Example 1

When 5 g of the compound from Production Example 1, 895 g of lactose and 100 g of corn starch are mixed together, a powder preparation is obtained.

PREPARATION EXAMPLE 2

Granules Comprising the Compound from Production Example 1

After mixing 5 g of the compound from Production Example 1, 865 g of lactose and 100 g of hydroxypropyl cellulose of low degree of substitution, 300 g of 10% aqueous hydroxypropyl cellulose solution is added and kneading performed. The mixture is extruded and granulated using a granulator, and then dried to obtain a granular preparation (granules).

PREPARATION EXAMPLE 3

Capsules of the Compound of Production Example 1

After mixing together 5 g of the compound from Production Example 1, 115 g of lactose, 58 g of corn starch and 2 g of magnesium stearate using a V-shape mixer, No. 3 capsule containers are filled with 180 mg quantities of the mixture and capsules obtained.

PREPARATION EXAMPLE 4

Tablets of the Compound of Production Example 1

After mixing together 5 g of the compound from Production Example 1, 90 g of lactose, 34 g of corn starch, 20 g of crystalline cellulose and 1 g of magnesium stearate in a blender, tableting is carried out with a tableting machine and tablets obtained.

INDUSTRIAL APPLICATION POTENTIAL

The drugs of the present invention which contain a compound of general formula (I) are outstanding in their action in suppressing the fall in MTT reduction capacity brought about by β-amyloid protein, and in inhibiting impairment of long-term potentiation of hippocampal nerve cells, so they are useful as preventatives or remedies for Alzheimer's disease.

The amyloid protein fibril-formation inhibitors of the present invention are outstanding in their action in inhibiting amyloid protein fibril-formation and in their fibrillar amyloid protein breakdown action, so they are valuable as preventatives or remedies for amyloidosis, such as Alzheimer's disease, type 2 diabetes, immunoglobulinic amyloidosis, reactive amyloidosis, familial amyloidosis, dialysis-related amyloidosis, senile amyloidosis, cerebrovascular amyloidosis, hereditary cerebral hemorrhage with amyloidosis, Creutzfeldt-Jakob disease, bovine spongiform encephalitis (BSE), scrapie, medullary carcinoma of the thyroid, insulinoma, localized atrial amyloid, amyloidosis cutis and localized nodular amyloidosis, preferably for Alzheimer's disease, type 2 diabetes, dialysis-related amyloidosis, familial amyloidosis, Creutzfeldt-Jakob disease and BSE, in particular for Alzheimer's disease and type 2 diabetes.

Furthermore, the nitrogen-containing heteroaryl derivatives of the present invention and their pharmacologically permitted salts are valuable as preventives or remedies for Alzheimer's disease of warm-blooded animals (in particular humans), or as amyloid protein fibril-formation inhibitors.

The invention claimed is:
1. A pharmaceutical composition which comprises, as an active ingredient, at least one nitrogen-containing heteroaryl compound represented by the following general formula (I) or pharmacologically permitted salt thereof, and a pharmacologically permitted diluent or other pharmacologically permitted additive:

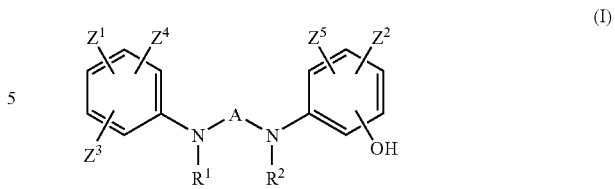

where
$R^1$ and $R^2$ each independently represent a hydrogen atom or a $C_{1-6}$ alkyl group,
$Z^1$ and $Z^2$ each independently represent a hydrogen atom, $C_{1-6}$ alkyl group, $C_{1-6}$ alkoxy group, halo-$C_{1-6}$ alkyl group or halogen atom,
$Z^3$ represents a $C_{1-6}$ alkoxy group, mercapto group, $C_{1-6}$ alkylthio group, amino group, mono- or di-$C_{1-6}$ alkylamino group, hydroxy group or halogen atom,
$Z^4$ and $Z^5$ each independently represent a hydrogen atom or halogen atom, and
A represents a group of formula V below

where
$R^9$ represents a $C_{1-6}$ alkyl group, $C_{1-6}$ alkoxy group, mercapto group, $C_{1-6}$ alkylthio group, or hydroxy group.

2. A nitrogen-containing heteroaryl compound represented by the following general formula (VII) or pharmacologically permitted salt thereof;

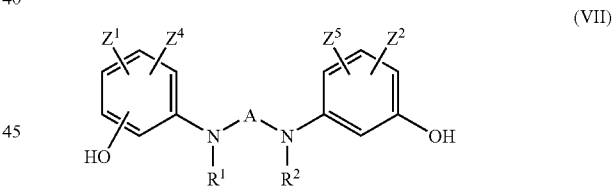

where $R^1$ and $R^2$ each independently represent a hydrogen atom or $C_{1-6}$ alkyl group,
$Z^1$ and $Z^2$ each independently represent a hydrogen atom, $C_{1-6}$ alkyl group, $C_{1-6}$ alkoxy group, halogen atom or halo-$C_{1-6}$ alkyl group,
$Z^4$ and $Z^5$ each independently represent a hydrogen atom or halogen atom, and
A represents a group of formula V:

where
R$^9$ represents a C$_{1-6}$ alkyl group, C$_{1-6}$ alkoxy group, mercapto group, C$_{1-6}$ alkylthio group, mono- or di-C$_{1-6}$ alkylamino group or hydroxy group.

3. A nitrogen-containing heteroaryl derivatives compound or pharmacologically permitted salts thereof according to claim 2, where R$^1$ and R$^2$ are each independently a hydrogen atom or C$_{1-2}$ alkyl group.

4. A nitrogen-containing heteroaryl compound or pharmacologically permitted salts thereof according to claim 2, where R$^1$ and R$^2$ are hydrogen atoms.

5. A nitrogen-containing heteroaryl compound or pharmacologically permitted salts thereof according to claim 2, where A is a group of formula (V) where R$^9$ is a C$_{1-5}$ alkyl, C$_{1-4}$ alkoxy or a C$_{1-4}$ alkylthio group.

6. A nitrogen-containing heteroaryl compound or pharmacologically permitted salts thereof according to claim 2, where A is a group of formula (V) where R$^9$ is a C$_{2-4}$ alkyl group.

7. A nitrogen-containing heteroaryl compound or pharmacologically permitted salts thereof according to claim 2, where A is a group of formula (V) where R$^9$ is a C$_{2-4}$ alkyl group.

8. A nitrogen-containing heteroaryl compound or pharmacologically permitted salts thereof according to claim 2, where Z$^1$ and Z$^2$ are each independently a hydrogen atom or para-position fluorine atom, chlorine atom or C$_{1-2}$ alkyl group, the hydroxy group on the phenyl ring to which Z$^1$ is bonded is in the meta-position, and Z$^4$ and Z$^5$ are hydrogen atoms.

9. A nitrogen-containing heteroaryl compound or pharmacologically permitted salts thereof according to claim 2, where Z$^1$ and Z$^2$ are hydrogen atoms or para-position methyl groups, the hydroxy group on the phenyl ring to which Z$^1$ is bonded is in the meta-position, and Z$^4$ and Z$^5$ are hydrogen atoms.

10. A nitrogen-containing heteroaryl compound according to claim 2 which is selected from any of the following, or pharmacologically permitted salt thereof;
   6-ethyl-N,N'-bis(3-hydroxyphenyl)-1,3,5-triazine-2,4-diamine,
   N,N'-bis(3-hydroxyphenyl)-6-propyl-1,3,5-triazine-2,4-diamine,
   6-isobutyl-N,N'-bis(3-hydroxyphenyl)-1,3,5-triazine-2,4-diamine,
   6-s-butyl-N,N'-bis(3-hydroxyphenyl)-1,3,5-triazine-2,4-diamine,
   6-t-butyl-N,N'-bis(3-hydroxyphenyl)-1,3,5-triazine-2,4-diamine, and
   6-ethyl-N,N'-bis(3-hydroxy-4-methylphenyl)-1,3,5-triazine-2,4-diamine.

11. A pharmaceutical composition which comprises, as an actice ingredient, a nitrogen-containing heteroary compound according to claim 2, or pharmacologically permitted salt therof, and a pharmacologically permitted diluent or other pharmacologically permitted additive.

* * * * *

UNITED STATES PATENT AND TRADEMARK OFFICE
CERTIFICATE OF CORRECTION

| | | |
|---|---|---|
| PATENT NO. | : 8,003,645 B2 | Page 1 of 1 |
| APPLICATION NO. | : 12/068407 | |
| DATED | : August 23, 2011 | |
| INVENTOR(S) | : Meguro et al. | |

It is certified that error appears in the above-identified patent and that said Letters Patent is hereby corrected as shown below:

Column 47, line 17, after "alkyl" please insert --or a butoxy--.

Signed and Sealed this

Thirteenth Day of December, 2011

David J. Kappos
*Director of the United States Patent and Trademark Office*